(12) United States Patent
Wu et al.

(10) Patent No.: US 9,474,774 B2
(45) Date of Patent: Oct. 25, 2016

(54) PYRIDINE ALKALOIDS, PREPARATION PROCESS THEREOF, AND THE USES OF THE PYRIDINE ALKALOIDS

(75) Inventors: Ming-Der Wu, Hsinchu (TW); Ming-Jen Cheng, Hsinchu (TW); Shie-Jea Lin, Hsinchu (TW); Chi-Hua Chen, Hsinchu (TW); Yen-Lin Chen, Hsinchu (TW); Hui-Ping Chen, Hsinchu (TW); Kai-Ping Chen, Hsinchu (TW); Ping-Shin Yang, Hsinchu (TW); Shiow-Wen Chen, Hsinchu (TW); Gwo-Fang Yuan, Hsinchu (TW)

(73) Assignee: FOOD INDUSTRY RESEARCH AND DEVELOPMENT INSTITUTE, Hsinchu (TW)

( * ) Notice: Subject to any disclaimer, the term of this patent is extended or adjusted under 35 U.S.C. 154(b) by 465 days.

(21) Appl. No.: 12/981,915

(22) Filed: Dec. 30, 2010

(65) Prior Publication Data
US 2011/0165186 A1 Jul. 7, 2011

Related U.S. Application Data

(60) Provisional application No. 61/291,971, filed on Jan. 4, 2010.

(51) Int. Cl.
| | | |
|---|---|---|
| *A61K 45/06* | (2006.01) | |
| *A61K 36/062* | (2006.01) | |
| *A61K 31/44* | (2006.01) | |
| *C07D 213/80* | (2006.01) | |
| *C12P 17/12* | (2006.01) | |
| *C12R 1/645* | (2006.01) | |

(52) U.S. Cl.
CPC ............ *A61K 36/062* (2013.01); *A61K 31/44* (2013.01); *A61K 45/06* (2013.01); *C07D 213/80* (2013.01); *C12P 17/12* (2013.01); *C12R 1/645* (2013.01)

(58) Field of Classification Search
None
See application file for complete search history.

(56) References Cited

FOREIGN PATENT DOCUMENTS

IT WO 2006016383 A2 * 2/2006 .............. A23L 1/28

OTHER PUBLICATIONS

Akihisha et al. "(+)- and (−)-syn-2-lsobutyl-4-methylazetidine-2,4-dicarboxylic Acids from the Extract of Monascus pilosus-Fermented Rice (Red-Mold Rice)". J. Nat. Prod. vol. 67 (2004) 479-480.*
Tsuji, K., et al., 1992, "Effects of two kinds of Koji on blood pressure in spontaneously hypertensive rats." Nippon. Nogeikagaku Kaishi., 66: 1241-1246.
Endo, A., 1979, "Monacolin K, a new hypocholesterolemic agent produced by a *Monascus* species." J. Anthiot., 32: 852-854.
Endo, A., 1985, "Compactin (ML-236B) and related compounds as potential cholesterol-lowering agents that inhibit HMG-CoA reductase." J. Med. Chem., 28: 401-405.
Martinokova, L., et al., 1995, "Biological activity of polyketide pigments produced by the fungus Monascus." J. Appl. Bacteriol., 79: 609-616.
Chen, W-P. et al., 2008, "Red mold rice prevents the development of obesity, dyslipidemia and hyperinsulinemia induced by high-fat diet." International Journal of Obesity, 32: 1694-1704.
Shi, Y. and Pan, T., J. 2010, "Anti-diabetic effects of Monascus purpurcus NTU 568 fermented products on streptozotocin-induced diabetic rats." J. Agric. Food Chem., 58(13): 7634-7640.
Waki et al., 2007, "The small molecule harmine is an antidiabetic cell-type-specific regulator of PPAR? expression." Cell Metabolism, 5(5): 357-370.
Huang et al., 2005, "Herbal or natural medicines as modulators of peroxisome proliferator-activated receptors and related nuclear receptors for therapy of metabolic syndrome." Basic and Clinical Pharmacology and Toxicology, 96: 3-14.

* cited by examiner

*Primary Examiner* — Amy L Clark
(74) *Attorney, Agent, or Firm* — Ladas & Parry LLP

(57) ABSTRACT

The present invention relates to novel pyridine alkaloid compounds of formula (I):

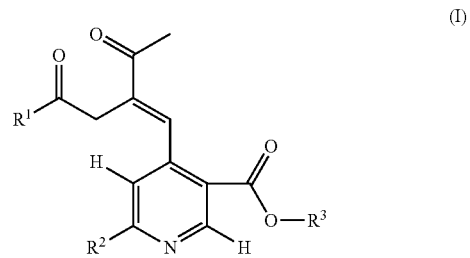

or a pharmaceutically acceptable derivative thereof as described in the specification, the process for the preparation of the same, and the composition comprising the same. The uses of a pyridine compound for increasing the activity of PPARγ, for the prevention and/or treatment of a disease or disorder related to insulin resistance, and for the prevention and/or treatment of metabolic syndrome or its complication are also provided. The invention also provides extracts of red yeast-fermented products and their uses for prevention and/or treatment of a disease or disorder related to insulin resistance, such as metabolic syndrome.

23 Claims, 11 Drawing Sheets

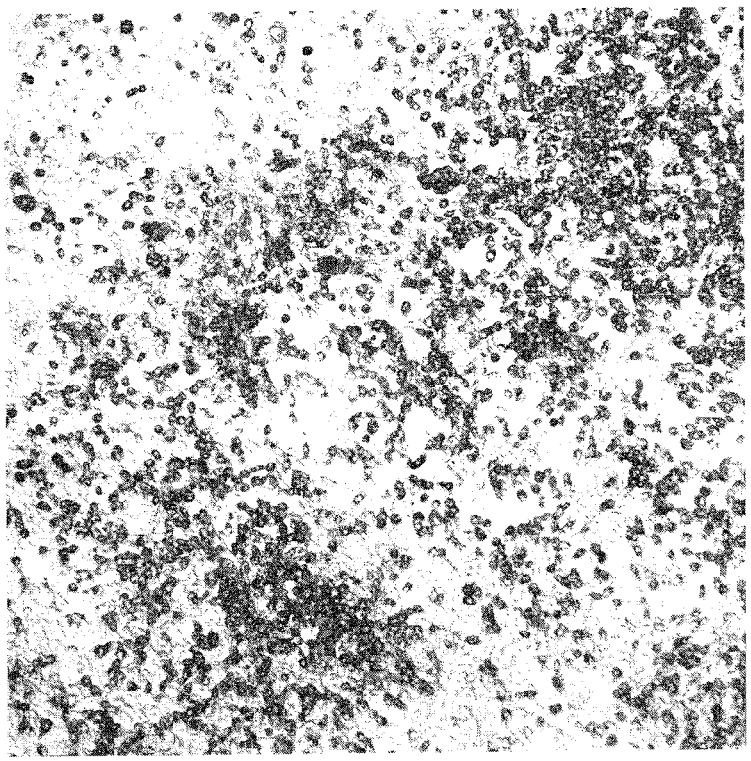
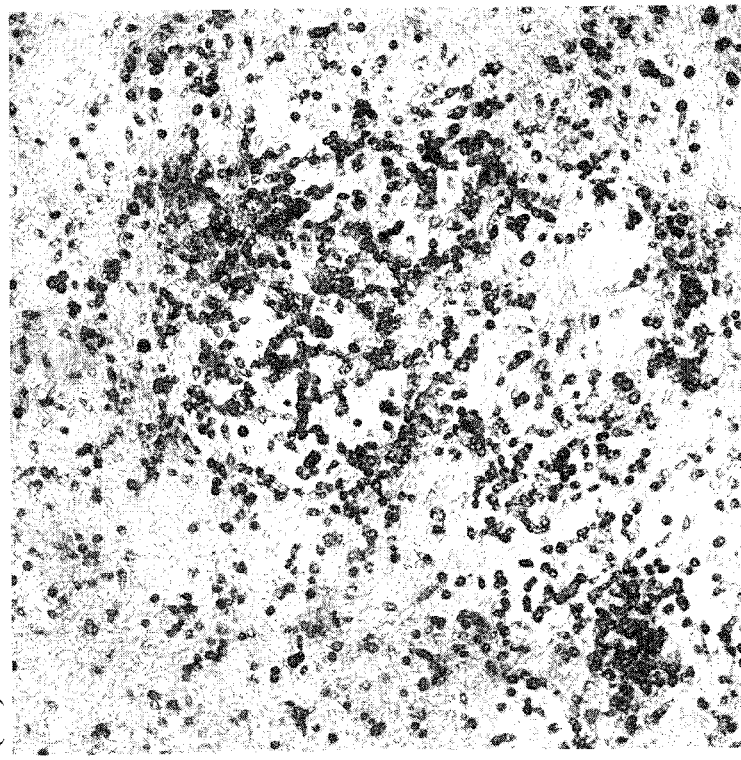
Figure 6 (A)-(B)

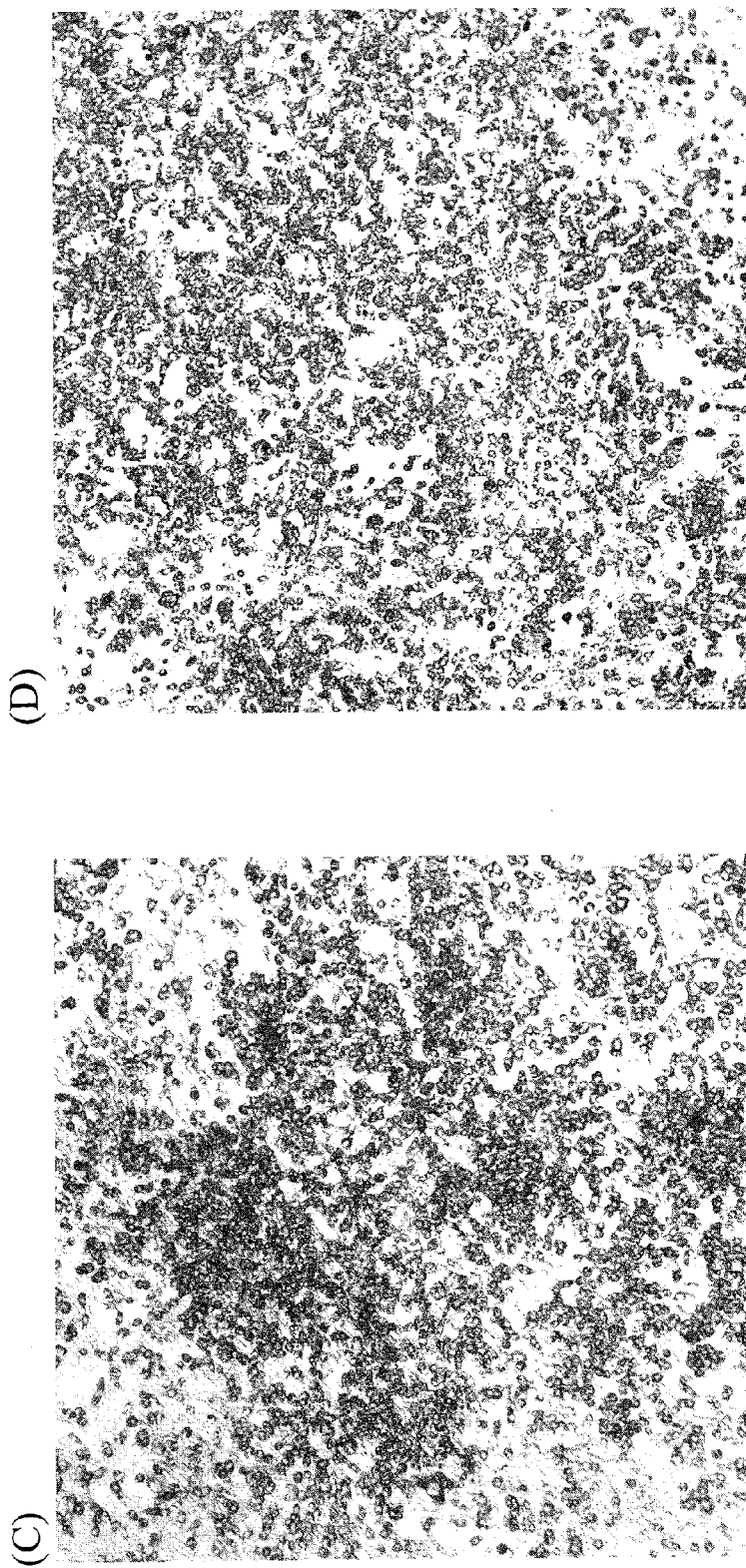
Figure 6 (C)-(D)

PYRIDINE ALKALOIDS, PREPARATION PROCESS THEREOF, AND THE USES OF THE PYRIDINE ALKALOIDS

CROSS REFERENCE TO RELATED APPLICATIONS

This application claims priority to U.S. Provisional Application Nos. 61/291,971, filed 4 Jan. 2010; the disclosure of which is incorporated herein by reference in its entirety.

FIELD OF THE INVENTION

This invention relates to the novel pyridine alkaloids and the process for the preparation of the same. It further relates to the compositions comprising a pyridine compound, and the use of a pyridine compound for the activation of PPARγ and for the prevention and/or treatment of a disease or disorder related to insulin resistance, such as metabolic syndrome. The invention also relates to the use of extracts of red yeast-fermented products for prevention and/or treatment of a disease or disorder related to insulin resistance, such as metabolic syndrome.

BACKGROUND OF THE INVENTION

*Monascus* spp. has been used in Chinese fermented foods for thousands of years. Red yeast rice fermented with *Monascus* spp. produces, in addition to some pigments, bioactive metabolites such as γ-aminobutyric acid (GABA) and polyketides monacolin K, which are used as an anti-hypertension agent (see Tsuji, K., et al., 1992, "Effects of two kinds of Koji on blood pressure in spontaneously hypertensive rats." *Nippon. Nogeikagaku Kaishi.,* 66: 1241-1246) and a cholesterol-lowering drug (see Endo, A., 1979, "Monacolin K, a new hypocholesterolemic agent produced by a *Monascus* species." *J. Antbiot.,* 32: 852-854; Endo, A., 1985, "Compactin (ML-236B) and related compounds as potential cholesterol-lowering agents that inhibit HMG-CoA reductase." *J. Med. Chem.,* 28: 401-405; and Martinokova, L., et al., 1995, "Biological activity of polyketide pigments produced by the fungus *Monascus.*" *J. Appl. Bacteriol.,* 79: 609-616), respectively.

Chen, W-P. et al. ("Red mold rice prevents the development of obesity, dyslipidemia and hyperinsulinemia induced by high-fat diet." *International Journal of Obesity,* 2008, 32: 1694-1704) reports that red yeast rice extracts can prevent the development of obesity, dyslipidemia and hyperinsulinemia induced by high-fat diet. The results show that water extract and ethanol extract of red yeast rice fermented by *Monascus purpureus* NTU 568 inhibit the proliferation of 3T3-L1 preadipocytes and inhibit the differentiation of 3T3-L1 preadipocytes to adipocytes. It is concluded that these effects probably resulted from an increase in the lipolysis activity of adipose tissue and a reduction in food/energy consumption.

The anti-diabetic effects of red yeast-fermented products were also reported (see Shi, Y. and Pan, T., J. 2010, "Anti-diabetic effects of *Monascus purpureus* NTU 568 fermented products on streptozotocin-induced diabetic rats." *J. Agric. Food Chem.,* 58(13): 7634-7640). However, the compounds in the red yeast-fermented products that have the anti-diabetic effects and their pharmacological mechanism are unknown.

Modulating lipid metabolism is one of the strategies of the treatment of metabolic syndrome. Thiazolidinediones (TZDs) are type 2 diabetes drugs developed in early 1980. Studies on mechanisms of TZDs shows that they increase insulin sensitivity by activating PPARγ. One of the characteristic effects of activating PPARγ is to increase differentiation of adipocytes. Increasing adipocyte differentiation has therefore become a popular method for screening agents that have potential in activating PPARγ and decreasing insulin resistance.

SUMMARY OF THE INVENTION

One of the purposes of the invention is to provide a compound of formula (I):

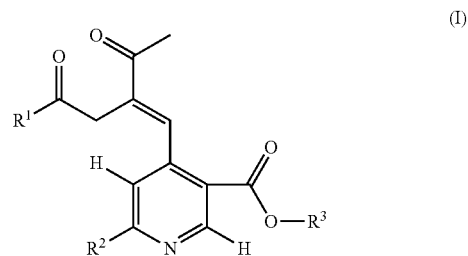

(I)

or a pharmaceutically acceptable derivative thereof, wherein $R^1$ is alkyl, $R^2$ is alkyl or alkenyl, and $R^3$ is alkyl.

Another purpose of the present invention is to provide a composition comprising the compound of formula (I) or a pharmaceutically acceptable derivative thereof, and optionally a pharmaceutically acceptable carrier or excipient.

Another purpose of the present invention is to provide a process for the preparation of the compound of formula (I) or a pharmaceutically acceptable derivative thereof.

Another purpose of the present invention is to provide a red yeast rice extract.

Another purpose of the present invention is to provide a composition comprising the red yeast rice extract of the invention, and optionally a pharmaceutically acceptable carrier or excipient.

Another purpose of the present invention is to provide a method for increasing the activity of PPARγ.

Another purpose of the present invention is to provide a method of preventing and/or treating a disease or disorder related to insulin resistance in a subject.

Still another purpose of the present invention is to provide a method of preventing and/or treating metabolic syndrome or its complications.

The present invention is described in detail in the following sections. Other characteristics, purposes and advantages of the present invention can be easily found in the detailed descriptions and claims.

DETAILED DESCRIPTION OF THE INVENTION

Figure 1:
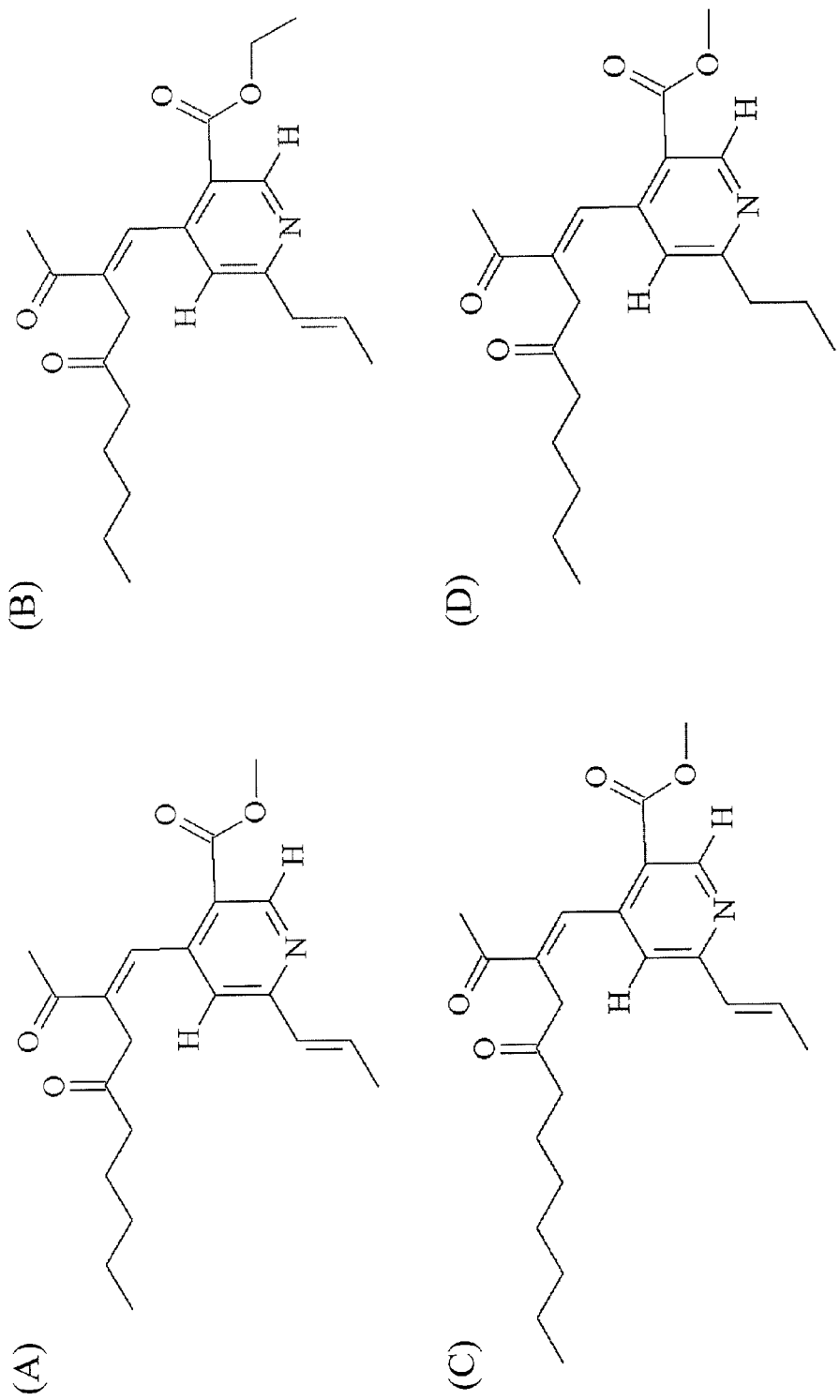
FIG. 1 shows the structures of (A) Monasnicotinate A, (B) Monasnicotinate B, (C) Monasnicotinate C, and (D) Monasnicotinate D.

The present invention can be understood more readily by reference to the following detailed description of various embodiments of the invention, the examples, and the chemical drawings and tables with their relevant descriptions. Before the present compounds, compositions, and/or methods are disclosed and described, it is to be understood that unless otherwise specifically indicated by the claims, the invention is not limited to specific preparation methods, carriers or formulations, or to particular modes of formulating the compounds of the invention into products or compositions intended for topical, oral or parenteral administration, because as one of ordinary skill in relevant arts is well aware, such things can, of course, vary. It is also to be understood that the terminology used herein is for the purpose of describing particular embodiments only and is not intended to be limiting.

DEFINITIONS

As utilized in accordance with the present disclosure, the following terms, unless otherwise indicated, shall be understood to have the following meanings:

As used herein, the terms "alkyl" and "alkenyl" include straight and branched chains.

"Alkyl" refers to a hydrocarbon group that can be conceptually formed from an alkane by removing hydrogen from the structure of a non-cyclic hydrocarbon compound having straight or branched carbon chains, and replacing the hydrogen atom with another atom or organic or inorganic substituent group. In some embodiments of the invention, the alkyl groups are "$C_1$ to $C_{10}$ alkyl" such as methyl, ethyl, propyl, isopropyl, n-butyl, iso-butyl, sec-butyl, tert-butyl, amyl, tert-amyl, hexyl and the like. Many embodiments of the invention comprise "$C_1$ to $C_7$ alkyl" groups that include methyl, ethyl, propyl, iso-propyl n-butyl, iso-butyl, sec-butyl, t-butyl, pentyl, hexyl, and heptyl groups.

The term "alkenyl" is structurally analogous to an alkyl group or residue that comprises at least one carbon-carbon double bond. In some embodiments, the alkenyl groups are "$C_2$ to $C_7$ alkenyls" which are exemplified by vinyl, allyl, propenyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, and 6-heptenyl, as well as dienes and trienes of straight and branched chains. In other embodiments, alkenyls are limited to two to four carbon atoms.

The term "a pharmaceutically acceptable derivative" or "pharmaceutically acceptable derivatives" as used herein denotes a compound that is modified from the compound of the invention but has properties and efficacies that are the same as or better than those of the compound of the invention. Preferably, the pharmaceutically acceptable derivative is a pharmaceutically acceptable salt, solvate, hydrate, or prodrug of the compound of the invention.

One or more of the compounds of the invention may be present as a salt. The term "salt" encompasses those salts formed with the organic and inorganic anions and cations. Furthermore, the term includes salts that form by standard acid-base reactions with basic groups and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, and cinnamic acids.

The compounds of the invention can also exist as solvates and hydrates. Thus, these compounds may crystallize with, for example, waters of hydration, or one, a number of, or any fraction of molecules of the mother liquor solvent. The solvates and hydrates of such compounds are included within the scope of this invention.

The term "subject" as used herein denotes any animal, preferably a mammal, and more preferably a human. Examples of subjects include humans, non-human primates, rodents, guinea pigs, rabbits, sheep, pigs, goats, cows, horses, dogs and cats.

The term "effective amount" of a compound as provided herein means a sufficient amount of the compound to provide the desired regulation of a desired function, such as gene expression, protein function, or the induction of a particular type of response. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "preventing" or "prevention" is recognized in the art, and when used in relation to a condition, it includes administering, prior to onset of the condition, an agent to reduce the frequency or severity of or delay the onset of symptoms of a medical condition in a subject relative to a subject which does not receive the agent.

The term "treating" or "treatment" as used herein denotes reversing, alleviating, inhibiting the progress of, or improving the disorder or condition to which such term applies, or one or more symptoms of such disorder or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint.

"Optional" or "optionally" means that the subsequently described event or circumstance may or may not occur, and that the description includes instances where said event or circumstance occurs and instances where it does not. For example, the phrase "optionally comprise an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The Compounds of the Invention

The present invention relates to pyridine alkaloids or a pharmaceutically acceptable derivative thereof. The pyridine alkaloids of the invention have the following formula (I):

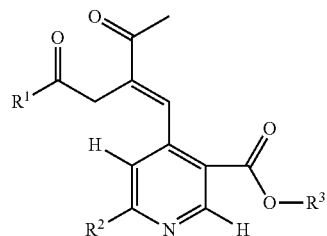

wherein $R^1$ is alkyl, $R^2$ is alkyl or alkenyl, and $R^3$ is alkyl.

In some embodiments of the compound of formula (I), $R^1$ is $C_1$-$C_{10}$alkyl, $R^2$ is $C_1$-$C_6$alkyl or $C_2$-$C_6$alkenyl, and $R^3$ is $C_1$-$C_6$alkyl.

In a preferred embodiment, $R^1$ is pentyl, $R^2$ is propenyl, and $R^3$ is methyl.

In another preferred embodiment, $R^1$ is pentyl, $R^2$ is propenyl, and $R^3$ is ethyl.

In another preferred embodiment, $R^1$ is heptyl, $R^2$ is propenyl, and $R^3$ is methyl.

In another preferred embodiment, $R^1$ is pentyl, $R^2$ is propyl, and $R^3$ is methyl.

In a most preferred embodiment, the compound of formula (I) methyl-4-((E)-2-acetyl-4-oxonon-1-enyl)-6-((E)-prop-1-enyl)nicotinate (Monasnicotinate A), ethyl-4-((E)-2-acetyl-4-oxonon-1-enyl)-6-((E)-prop-1-enyl)nicotinate (Monasnicotinate B), methyl-4-((E)-2-acetyl-4-oxoundec-1-enyl)-6-((E)-prop-1-enyl)nicotinate (Monasnicotinate C), or (E)-methyl-4-(2-acetyl-4-oxonon-1-enyl)-6-propylnicotinate (Monasnicotinate D).

The compounds of the invention can be further converted into a pharmaceutically acceptable derivative, such as a pharmaceutically acceptable salt, solvate or prodrug, by any known methods.

The Compositions of the Invention

The present invention also provides a composition comprising the compound of the invention or a pharmaceutically acceptable derivative thereof. The composition of the invention can be a food composition or a pharmaceutical composition. The compound of formula (I) of the present invention in the composition can be provided in the form of an extract of red yeast rice or a chemical compound.

The pharmaceutical composition of the invention can be administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art. In the present invention, the pharmaceutical composition can be formulated in various ways, according to the corresponding route of administration, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof. If necessary, it may be sterilized or mixed with any pharmaceutically acceptable carrier or excipient, many of which are known to one of ordinary skill in the art.

The Preparation Processes of the Invention

The present invention provides processes for the preparation of the compound of formula (I):

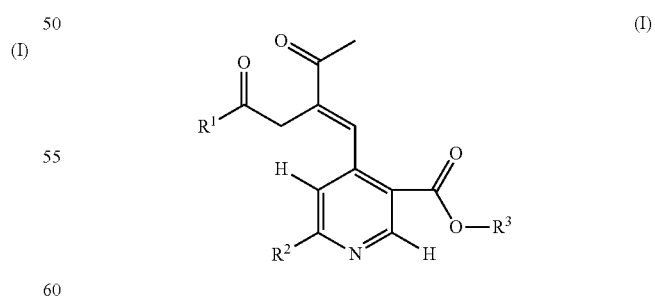

or a pharmaceutically acceptable derivative thereof, wherein $R^1$ is alkyl, $R^2$ is alkyl or alkenyl, and $R^3$ is alkyl.

In one preferred embodiment, the process of the invention comprises the steps of:

(a) fermenting rice with the isolated strain of Monascus spp. to obtain red yeast rice;

(b) extracting the red yeast rice with methanol or ethanol;

(c) extracting the extract obtained in step (b) between ethyl acetate and $H_2O$ to obtain an ethyl acetate-soluble fraction;

(d) eluting the ethyl acetate-soluble fraction through a silica gel chromatographic column with eluents; and (e) purifying the eluted fraction of (d) with silica gel chromatographic column and/or preparative thin layer chromatography (TLC) to obtain the compound.

According to the process of the invention, the isolated strain can be *Monascus pilosus*, *Monascus purpureus* or *Monascus ruber*, preferably *Monascus pilaw* or *Monascus purpureus*, more preferably *Monascus pilosus* BCRC 930117 (DSM 22351) or *Monascus purpureus* M615 BCRC 930146 (DSM 24162).

According to the process of the invention, prior to step (b), the red yeast rice can be dried.

According to the process of the invention, the ratio of ethyl acetate and $H_2O$ in step (c) is about 1:1.

According to the process of the invention, step (d) comprises loading the ethyl acetate-soluble fraction into a chromatographic column with silica gel and eluting the column with an eluent comprising n-hexane/ethyl acetate: 12:1, 10:1, 8:1, 6:1, 4:1, 2:1, 1:1, EA, EA/Methanol: 8:1, 6:1, 4:1, 2:1, 1:1, and methanol to produce thirty-two fractions. The eluted fraction used in step (e) is Fraction 10, 11 or 14.

According a preferred process of the invention, the purification method in step (e) is TLC with n-hexane/EtOAc, 2:1 as solvent.

According another preferred process of the invention, the purification method in step (e) is column chromatography on silica gel eluting with n-hexane/EA: 8:1, 6:1, 4:1, 2:1, 1:1 and EA (each 500 ml) to yield seven fractions (fractions 14.1 to 14.7) and purifying fraction 14.3 by preparative TLC (n-hexane/EtOAc, 2:1).

The present invention provides processes for the preparation of red yeast rice extracts. In one preferred embodiment, the process comprises the steps of:

(a) fermenting rice with an isolated strain of *Monascus* spp. to obtain red yeast rice; and (b) extracting the red yeast rice with methanol, ethanol or ethyl acetate.

According to the red yeast rice extract preparation process of the invention, the isolated strain can be *Monascus pilosus*, *Monascus purpureus* or *Monascus ruber*, preferably *Monascus pilosus* or *Monascus purpureus*, more preferably *Monascus pilosus* BCRC 930117 (DSM 22351) or *Monascus purpureus* M615 BCRC 930146 (DSM 24162).

According to the red yeast rice extract preparation process of the invention, prior to step (b), the red yeast rice can be dried.

Utilities

One aspect of the therapeutic method of the present invention is to increase PPARγ activities in a subject in need of such modulation, which comprises administering to said subject an effective amount of a compound of formula (I):

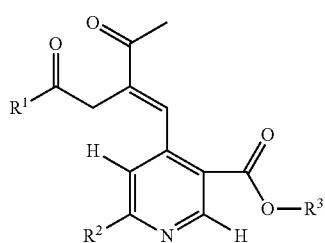

(I)

or a pharmaceutically acceptable derivative thereof, wherein $R^1$ is alkyl, $R^2$ is alkyl or alkenyl, and $R^3$ is alkyl, or a red yeast rice extract.

Another aspect of the therapeutic method of the present invention is to prevent and/or treat a disease or disorder related to insulin resistance in a subject, which comprises administering to said subject an effective amount of a compound of formula (I) or a pharmaceutically acceptable derivative thereof or a red yeast rice extract.

In certain embodiments, the disease or disorder related to insulin resistance is metabolic syndrome or its complications, such as atherogenic dyslipidemia, elevated blood pressure, insulin resistance or glucose intolerance, type 2 diabetes or cardiovascular disease.

According to the methods of the present invention, the compounds of formula (I) or a pharmaceutically acceptable derivative thereof can be administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art.

According to the methods of the present invention, the compounds of formula (I) or a pharmaceutically acceptable derivative thereof can be administered in combination with a second agent effective in preventing and/or treating metabolic syndrome or its complications, thereby improving the therapeutic effect of the compounds of the invention. Many agents are known in the art to be effective in preventing and/or treating metabolic syndrome or its complications. Examples of such agents include, but are not limited to, drugs to control cholesterol levels and lipids, such as statins, fibrates, or nicotinic acid; drugs to control high blood pressure, such as diuretics or angiotensin-converting enzyme (ACE) inhibitors; and drugs to control high blood sugar, such as metformin, insulin, sulfonylurea (SU), biguanide, α-glucosidase inhibitors, thiazolidinediones (TZDs) and the like.

The following examples are provided to aid those skilled in the art in practicing the present invention.

EXAMPLES

Microorganism

*Monascus pilosus* was deposited with the Bioresource Collection and Research Center (BCRC) of the Food Industry Research and Development Institute (FIRDI), 331 Shih-Pin Road, 300, Hsinchu, Taiwan, R.O.C., on 18 Feb. 2009 and assigned accession number BCRC 930117. It was also deposited with the Deutsche Sammlung von Mikroorganismen and Zellkulturen GmbH (DSMZ), Mascheroder Weg 1b, D38124, Braunschweig, Germany, on 5 Mar. 2009 in accordance with the Budapest Treaty and assigned accession number DSM 22351.

*Monascus purpureus* M615 used in Examples 7 to 10 was deposited with the BCRC of the FIRDI on 27 Oct. 2010 and assigned accession number BCRC 930146. It was also deposited with the DSMZ on 28 Oct. 2010 in accordance with the Budapest Treaty and assigned accession number DSM 24162.

Example 1

Preparation of Yeast Material

*M. pilosus* BCRC 930117 and *Monascus purpureus* M615 BCRC 930146 were inoculated on a Potato Dextrose Agar (PDA) (Difco, USA) plate and incubated at 30° C. for 7 days. The spores were washed out from the PDA plate using 6 ml of sterile water and 1 ml of the spore suspension was inoculated in a 250 ml Erlenmeyer flask containing GSP medium (which contains 7% of glycerol, 3% of flour, 1.2% of polypeptone, 3% of soybean powder, 0.1% of magnesium sulfate and 0.2% of sodium nitrate) and shook and incubated at 30° C., 150 rpm for three days to obtain the yeast material stock.

Example 2

Solid Fermentation

Ten 450-ml wide-mouth glass bottles each containing 75 g of Zailai rice (long grain rice) were added with 75 ml of 0.2% tartaric acid solution per bottle. The rice was soaked at 4° C. overnight. Then, the liquid was drained off and the rice was sterilized. An aliquot of 7.5 ml of the yeast material stock obtained in Example 1 was inoculated in each bottle and incubated at 25° C. for 14 days (at the 7th day of the incubation, 7.5 ml of GSP medium were added to the culture) to obtain red yeast rice.

Example 3

Extraction and Isolation of New Compounds from Red Yeast Rice

The red yeast rice of Example 2 was dried and 5 Kg of the dried red yeast rice was extracted three times with 95% EtOH (6 L) at room temperature. The ethanol syrup extract was partitioned between EtOAc and $H_2O$ (1:1) (10 L) to afford EtOAc (76 g) soluble fraction.

The EtOAc-soluble fraction was chromatographed over silica gel (75 g, 70-230 mesh) (Merck, Germany) and eluted with n-hexane/ethyl acetate: 12:1, 10:1, 8:1, 6:1, 4:1, 2:1, 1:1, EA, EA/Methanol: 8:1, 6:1, 4:1, 2:1, 1:1, and methanol (each 1 L) to produce thirty-two fractions. Fraction 10 was purified by preparative TLC (n-hexane/EtOAc, 2:1) to give new Compound A (36.4 mg). Fraction 11 was purified by preparative TLC (n-hexane/EtOAc, 2:1) to give new Compounds B (7.8 mg) and C (39.2 mg). Fraction 14 was further purified by column chromatography on silica gel eluting with n-hexane/EA: 8:1, 6:1, 4:1, 2:1, 1:1 and EA (each 500 ml) to yield seven fractions (fractions 14.1 to 14.7). Compound D (3.5 mg) was furnished from fraction 14.3 by preparative TLC (n-hexane/EtOAc, 2:1).

Example 4

Characterization of New Compounds

Extensive chromatographic purification of the EtOAc-soluble fraction of the EtOH extract of the red yeast rice of *M. pilosus* BCRC 930117 afforded four new compounds, Compounds A, B, C and D. The characterization of new compounds was conducted as follows.

Optical rotations were measured on a Jasco P-1020 digital polarimeter. UV spectra were obtained on a Jasco UV-240 spectrophotometer in MeOH, and IR spectra (KBr or neat) were taken on a Perkin-Elmer System 2000 FT-IR spectrometer. 1D ($^1H$, $^{13}C$, DEPT) and 2D (COSY, NOESY, HSQC, HMBC) NMR spectra using $CDCl_3$ as solvent were recorded on a Varian Unity Plus 400 (400 MHz for $^1H$ NMR, 100 MHz for $^{13}C$ NMR). Chemical shifts were internally referenced to the solvent signals in $CDCl_3$ ($^1H$, δ 7.26; $^{13}C$, δ 77.0) with TMS as the internal standard. High-resolution ESI-MS spectra were obtained on a Bruker Daltonics APEX II 30e spectrometer. Silica gel (70-230, 230-400 mesh) (Merck) was used for column chromatography, and silica gel 60 F-254 (Merck) was used for TLC and preparative TLC.

Characteristics of Compound A

New Compound A was obtained as white powder and has the following characteristics:

$^1H$ NMR ($CDCl_3$, 400 MHz): 0.88 (3H, t, J=6.8 Hz, $CH_3$-22), 1.27 (2H, m, $CH_2$-21), 1.32 (2H, m, $CH_2$-20), 1.59 (2H, m, $CH_2$-19), 1.96 (3H, dd, J=7.0, 1.8 Hz, $CH_3$-9), 2.51 (3H, s, 15-$COCH_3$), 2.54 (2H, d, J=7.4 Hz, $CH_2$-18), 3.27 (2H, s, $CH_2$-16), 3.92 (3H, s, $OCH_3$-12), 6.54 (1H, br d, J=12.0 Hz, H-7), 6.93 (1H, m, H-10), 7.33 (1H, s, H-5), 8.13 (1H, s, H-13), 9.13 (1H, s, H-2);

$^{13}C$ NMR ($CDCl_3$, 100 MHz): 13.9 (C-22), 18.6 (C-9), 22.4 (C-21), 23.4 (C-19), 25.4 (15-$COCH_3$), 31.3 (C-20), 40.6 (C-16), 43.2 (C-18), 52.3 (C-12), 120.1 (C-5), 121.1 (C-3), 130.2 (C-7), 135.4 (C-8), 136.9 (C-14), 140.9 (C-13), 145.7 (C-4), 151.83 (C-2), 159.4 (C-6), 165.5 (C-10), 198.8 (C-15), 208.7 (C-17);

IR (Neat) $cm^{-1}$: 1712, 1668 (C=O);
UV $\lambda_{max}$ (MeOH) nm (log ε): 253, 280, 330;
ESI-MS m/z 380 [M+Na]$^+$;
HR-ESI-MS m/z 380.1837 [M+Na]$^+$ (calcd for $C_{21}H_{27}NO_4Na$, 380.1835).

Characteristics of Compound B

New Compound B was isolated as yellow oil and has the following characteristics:

$^1H$ NMR ($CDCl_3$, 400 MHz): 0.87 (3H, t, J=7.2 Hz, $CH_3$-23), 1.32, 1.33, 1.59 (each 2H, m, $CH_2$-20~22), 1.39 (3H, t, J=7.2 Hz, $CH_3$-13), 1.95 (3H, dd, J=7.0, 2.0 Hz, $CH_3$-9), 2.50 (3H, s, 16-$COCH_3$), 2.54 (2H, d, J=7.4 Hz, $CH_2$-19), 3.27 (2H, s, $CH_2$-17), 4.36 (2H, q, J=7.2 Hz, $CH_2$-12), 6.54 (1H, br d, J=12.0 Hz, H-7), 6.92 (1H, m, H-8), 7.24 (1H, s, H-5), 8.12 (1H, s, H-14), 9.14 (1H, s, H-2);

$^{13}C$ NMR ($CDCl_3$, 100 MHz): 13.9 (C-23), 14.2 (C-13), 18.6 (C-9), 22.4 (C-21), 23.4 (C-19), 25.4 (15-$COCH_3$), 31.3 (C-21), 40.7 (C-17), 43.2 (C-19), 61.4 (C-12), 120.1 (C-5), 121.1 (C-3), 130.1 (C-7), 135.5 (C-8), 136.9 (C-15), 141.0 (C-14), 145.7 (C-4), 151.7 (C-2), 159.4 (C-6), 165.5 (C-10), 198.8 (C-16), 208.7 (C-18);

IR (Neat) $cm^{-1}$: 1716, 1676 (C=O);
UV $\lambda_{max}$ (MeOH) nm (log ε): 248, 275, 338;
ESI-MS m/z 394 [M+Na]$^+$;
HR-ESI-MS m/z 394.1994 [M+Na]$^+$ (calcd for $C_{22}H_{29}NO_4Na$, 394.1998).

Characteristics of Compound C

New Compound C was isolated as yellow oil and has the following characteristics:

$^1H$ NMR ($CDCl_3$, 400 MHz): 0.87 (3H, t, J=7.2 Hz, $CH_3$-24), 1.26 (8H, br s, $CH_2$-20~23), 1.58 (2H, m, $CH_2$-19), 1.95 (3H, dd, J=7.0, 2.0 Hz, $CH_3$-9), 2.50 (3H, s, 15-$COCH_3$), 2.53 (2H, t, J=7.2 Hz, $CH_2$-18), 3.27 (2H, s, $CH_2$-16), 3.92 (3H, s, $OCH_3$-12), 6.54 (1H, br d, J=12.0 Hz, H-7), 6.92 (1H, m, H-8), 7.24 (1H, s, 8.12 (1H, s, H-13), 9.14 (1H, s, H-2);

$^{13}C$ NMR ($CDCl_3$, 100 MHz): 14.1 (C-24), 18.7 (C-9), 22.6 (C-21), 23.8 (C-19), 25.4 (15-$COCH_3$), 29.1 (C-22), 31.6 (C-20), 40.7 (C-16), 43.3 (C-18), 52.4 (C-12), 120.2 (C-5), 121.1 (C-3), 130.2 (C-7), 135.6 (C-8), 137.0 (C-14), 140.9 (C-13), 145.8 (C-4), 151.8 (C-2), 159.4 (C-6), 165.6 (C-10), 198.8 (C-15), 208.7 (C-17);

IR (Neat) $cm^{-1}$: 1724, 1672 (C=O);
UV $\lambda_{max}$ (MeOH) nm (log ε): 251, 282, 327;
ESI-MS m/z 408 [M+Na]$^+$;

HR-ESI-MS m/z 408.2151 [M+Na]$^+$ (calcd for C$_{23}$H$_{31}$NO$_4$Na, 408.2153).

Characteristics of Compound D

New Compound D was isolated as yellow oil and has the following characteristics:

$^1$H NMR (CDCl$_3$, 400 MHz): 0.88 (3H, t, J=7.2 Hz, CH$_3$-22), 0.94 (3H, t, J=7.2 Hz, CH$_3$-9), 1.26 (4H, m, CH$_2$-20, 21), 1.57 (2H, m, CH$_2$-19), 1.75 (2H, sext, J=7.2 Hz, CH$_3$-8), 2.51 (3H, s, 15-COCH$_3$), 2.52 (2H, t, J=7.2 Hz, CH$_2$-18), 3.26 (2H, s, CH$_2$-16), 3.93 (3H, s, OCH$_3$-12), 7.23 (1H, s, H-5), 8.13 (1H, s, H-13), 9.16 (1H, s, H-2);

$^{13}$C NMR (CDCl$_3$, 100 MHz): 13.7 (C-9), 13.9 (C-22), 22.4 (C-21), 22.7 (C-8), 23.4 (C-19), 25.4 (15-COCH$_3$), 31.3 (C-20), 39.8 (C-7), 40.7 (C-16), 43.2 (C-18), 52.5 (C-12), 121.5 (C-3), 122.8 (C-5), 137.2 (C-14), 140.5 (C-13), 146.2 (C-4), 150.9 (C-2), 165.3 (C-10), 166.4 (C-6), 198.8 (C-15), 208.7 (C-17);

IR (Neat) cm$^{-1}$: 1716, 1665 (C=O);

UV $\lambda_{max}$ (MeOH) nm (log ε): 245, 271, 328;

ESI-MS m/z 382 [M+Na]$^+$;

HR-ESI-MS m/z 382.1994 [M+Na]$^+$ (calcd for C$_{21}$H$_{29}$NO$_4$Na, 382.1994).

Structure Elucidation of Compounds A, B, C and D

Compound A has the molecular formula C$_{21}$H$_{27}$NO$_4$, as determined by HR-ESI-MS data in combination with its $^1$H-NMR, $^{13}$C-NMR and DEPT, requiring 9 degrees of unsaturation. The IR spectrum revealed the presence of multiple carbonyls C=O (1712, 1668 cm$^{-1}$), one of which was by UV spectrum analysis ($\lambda_{max}$ 253, 280 and 330 nm) in conjugated with a pyridine. Eight of the nine degrees of unsaturation inherent in the formula were accounted by $^{13}$C-NMR as one conjugated carbonyl, one ketone, one ester carbonyl, a pair of double bond, and five olefinic carbons. Accordingly, the Compound A contained a single pyridine ring.

The $^1$H-/$^{13}$C-NMR spectra indicated seven quaternary C-atoms, five CH, five CH$_2$, and four Me groups. In the $^1$H-NMR spectrum, there were typical signals for one OMe groups at $\delta_H$ 3.92 (3H, s), one acetyl moiety at $\delta_H$ 2.51 (3H, s), signals of α-methylene protons of a ketone at $\delta_H$ 2.54 (2H, d, J=7.4 Hz) and 3.27 (2H, s), one β-methylene resonance of a ketone at $\delta_H$ 1.59 (2H, m), two signal for a pyridine olefinic proton at $\delta_H$ 7.33 (1H, s) and 9.13 (1H, s), as well as one (E)-double bond signals at $\delta_H$ 6.54 (1H, br d, J=12.0 Hz) and 6.93 (1H, m), indicating that Compound A was probably a pyridine ring moiety possessing a conjugated carbonyl ester group. The carbons of the pyridine derivative were assigned, from $^{13}$C-NMR and DEPT experiments, and there were resonances for three C=O functions [$\delta_C$ 198.8 (α,β-unsaturated C=O group); 165.5 (ester C=O group), and 208.7 (C=O)], one C=C bond [$\delta_C$ 130.2, 135.4], one vinyl methyl carbon [$\delta_C$ 18.6], one methoxyl group [$\delta_C$ 52.3], one acetyl methyl moiety [$\delta_C$ 25.4], and three aliphatic methylenes C-atoms [$\delta_C$ 20.0, 31.0, 34.6]. The above data of Compound A also pointed to a pyrrole ring moiety with those of similar compounds.

Figure 2:
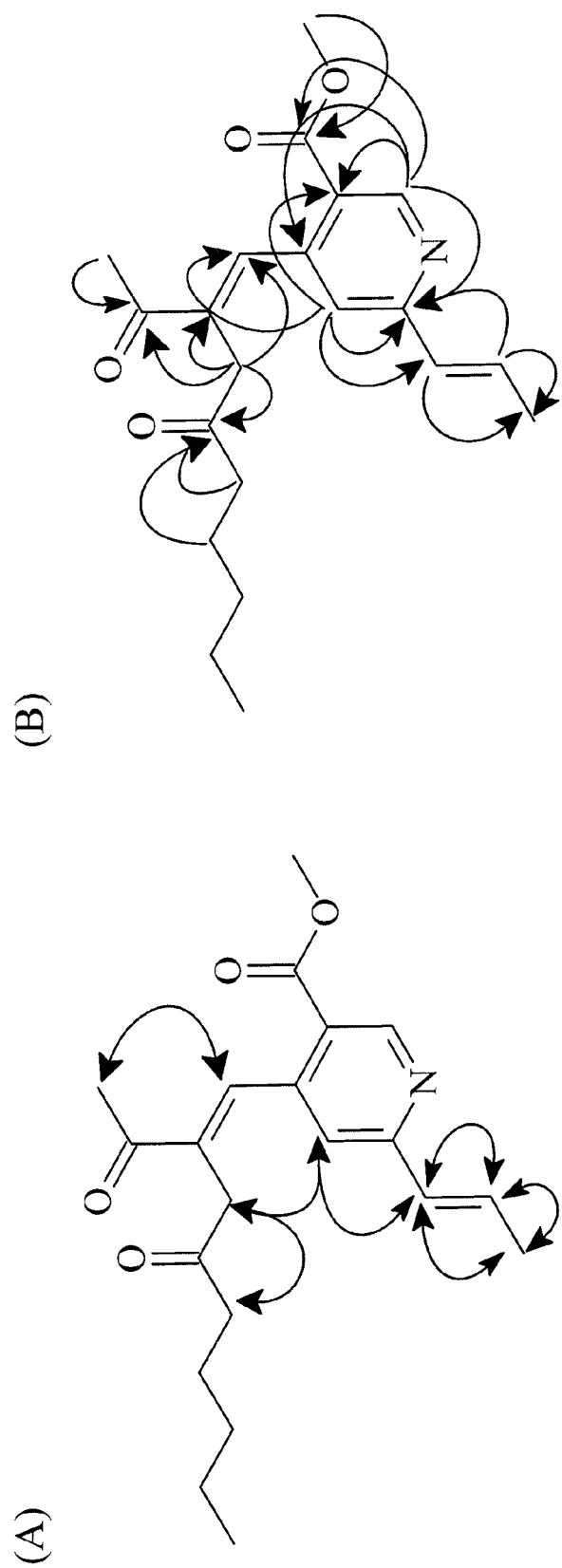
FIG. 2 shows the key (A) NOESY correlations and (B) HMBC correlations of Monasnicotinate A.

The structure of Compound A was further confirmed by $^{13}$C NMR, DEPT, COSY, NOESY (see FIG. 2A), HSQC, and HMBC (see FIG. 2B) experiments. The above observation accompanied by the $^1$H, $^1$H-COSY, and HMBC spectrum of Compound A established the presence of the partial three substitutes: fragments, 1a (—CH$_3$(CH$_2$)$_4$COCH$_2$C(=CH)(COCH$_3$)—, (E)-2-acetyl-4-oxonon-1-enyl), 1b (—CH=CHCH$_3$—, (E)-prop-1-enyl), and 1c (—COOCH$_3$—), for pyridine skeleton of compound A. The entire skeleton of Compound A was constructed by the aid of HMBC spectrum. Thus, the structure of Compound A was determined to be a methyl-4-((E)-2-acetyl-4-oxonon-1-enyl)-6-((E)-prop-1-enyl)nicotinate (see FIG. 1A), and was designated Monasnicotinate A.

Figure 3:
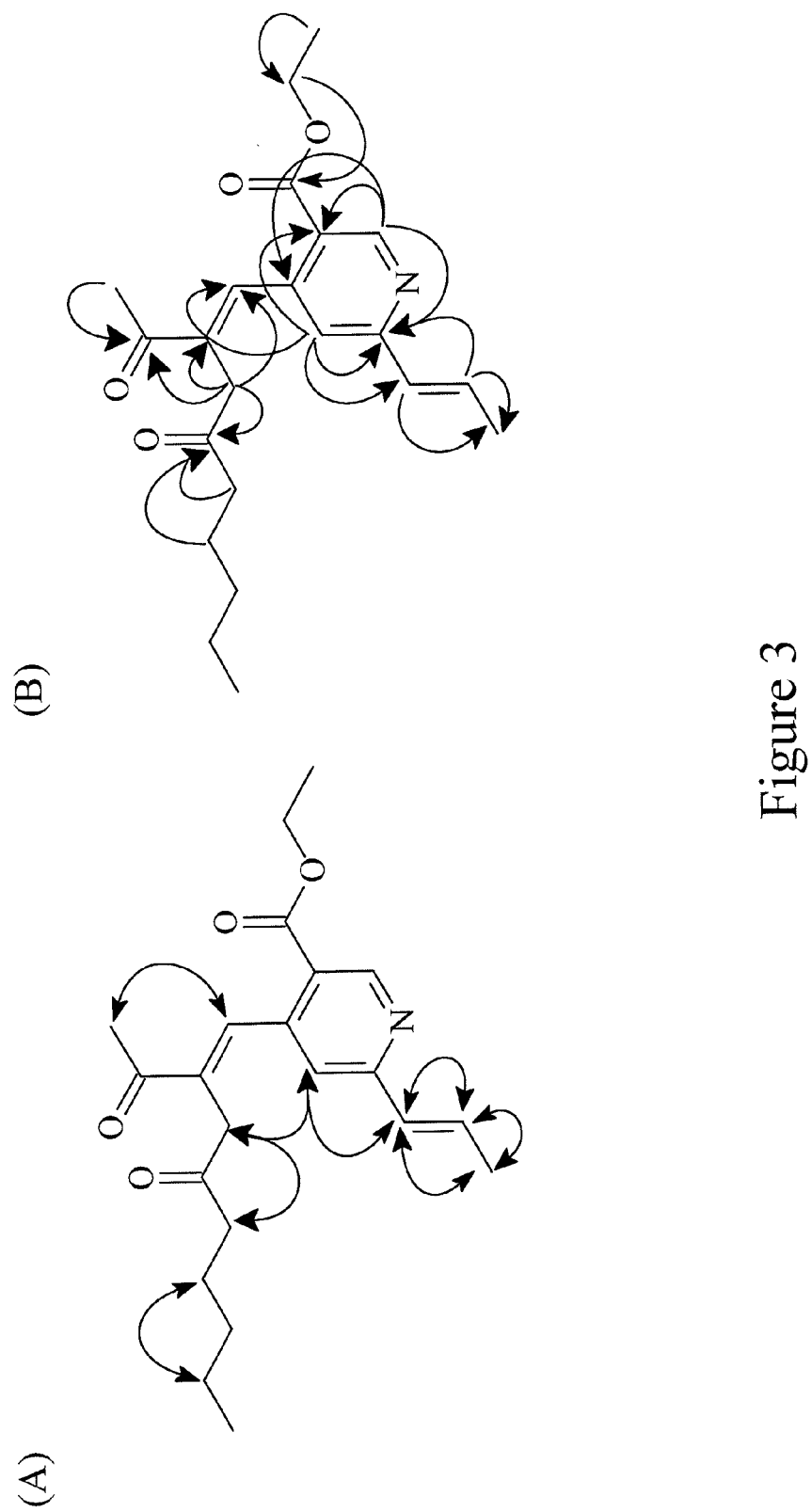
FIG. 3 shows the key (A) NOESY correlations and (B) HMBC correlations of Monasnicotinate B.
Figure 4:
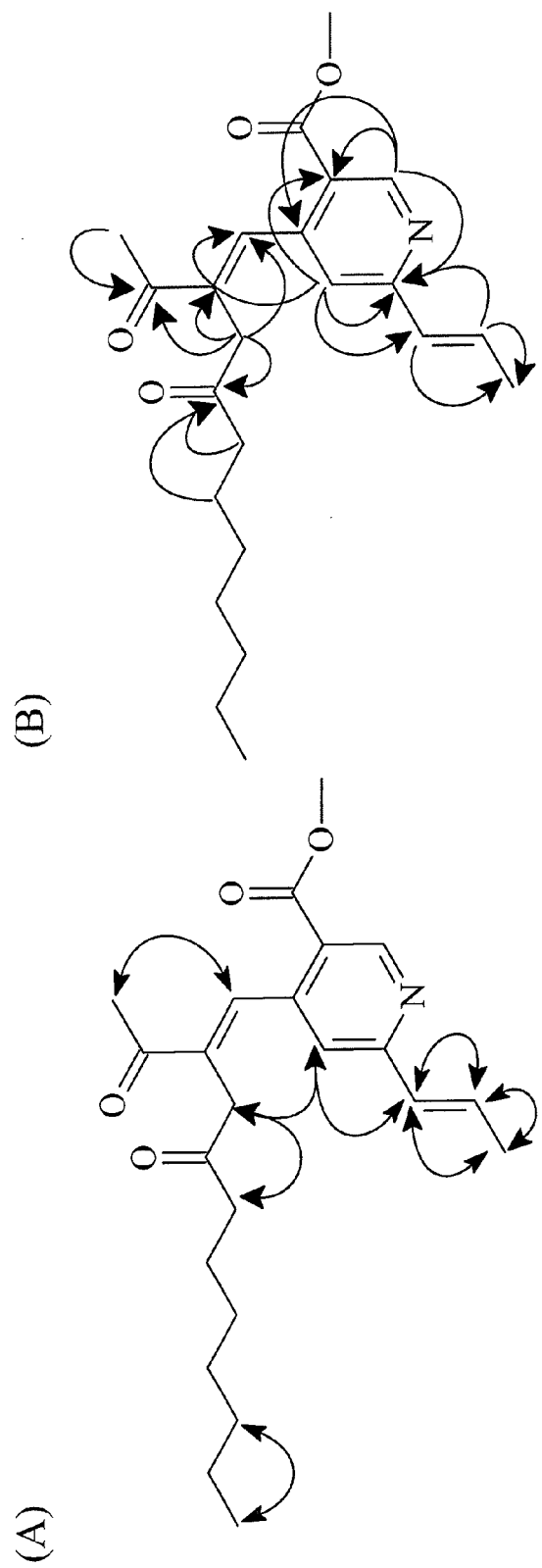
FIG. 4 shows the key (A) NOESY correlations and (B) HMBC correlations of Monasnicotinate C.
Figure 5:
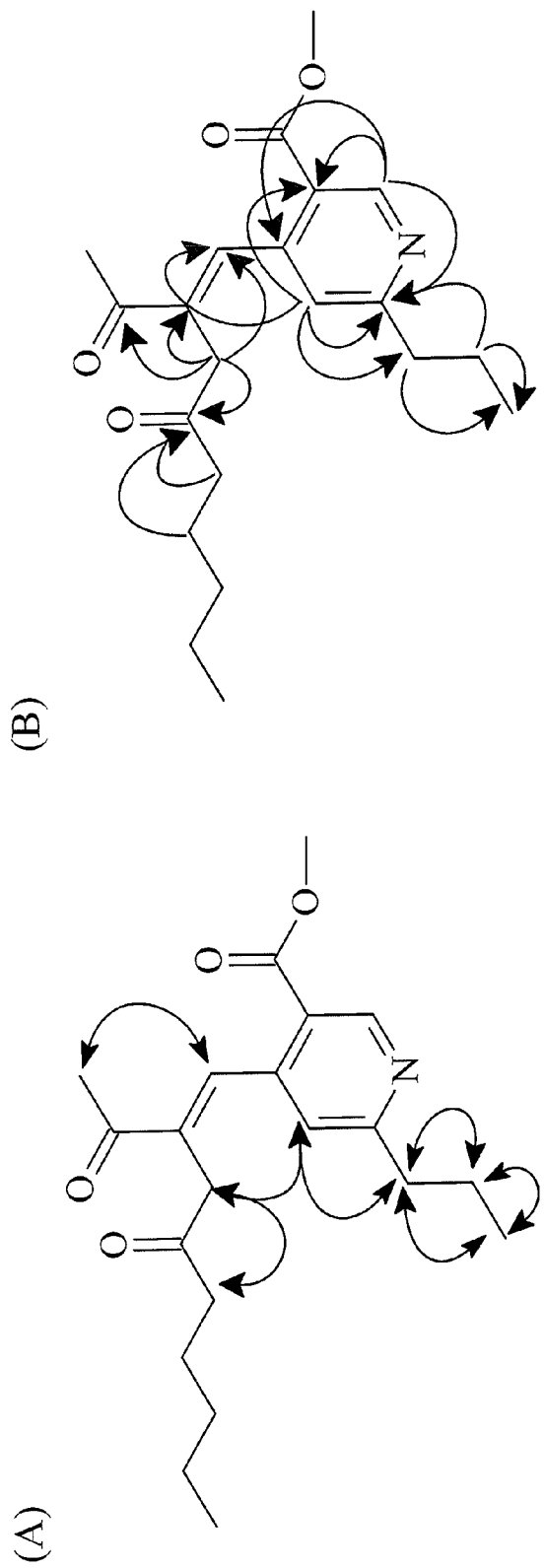
FIG. 5 shows the key (A) NOESY correlations and (B) HMBC correlations of Monasnicotinate D.

The $^1$H NMR spectrum of Compounds B to D was similar to Compound A, Monasnicotinate A, except that the substitutions at pyridine moiety were different. The structures were further confirmed by $^{13}$C NMR, DEPT, COSY, NOESY (see FIGS. 3A, 4A and 5A), HSQC, and HMBC (see FIGS. 3B, 4B and 5B) experiments. Thus, the structures of Compounds B, C and D were determined to be ethyl-4-((E)-2-acetyl-4-oxonon-1-enyl)-6-((E)-prop-1-enyl)nicotinate (see FIG. 1B), methyl-4-((E)-2-acetyl-4-oxoundec-1-enyl)-6-((E)-prop-1-enyl)nicotinate (see FIG. 1C), (E)-methyl-4-(2-acetyl-4-oxonon-1-enyl)-6-propylnicotinate (see FIG. 1D) and were designated as Monasnicotinates B, C and D, respectively.

Example 5

Monasnicotinates A, B, C and D Enhanced Adipocyte Differentiation in 3T3-L1 Cells Preparation of 3T3-L1 Preadipocytes Preadipocytes were prepared according to the method described by Waki et al., (2007, "The small molecule harmine is an antidiabetic cell-type-specific regulator of PPARγ expression." *Cell Metabolism*, 5(5): 357-370) and Huang et al., (2005, "Herbal or natural medicines as modulators of peroxisome proliferator-activated receptors and related nuclear receptors for therapy of metabolic syndrome." *Basic and Clinical Pharmacology and Toxicology*, 96: 3-14.). Preadipocytes were cultured in DMEM (Dulbecco's Modified Eagle's Medium-high glucose, Sigma D-7777) containing 10% of fetal bovine serum (FBS) and incubated at 37° C. in a 5% CO$_2$ incubator.

Before the differentiation induction experiments, the cells were plated into either 96- or 24-well plates (the concentration of cells in each well was about 2×10$^4$/cm$^2$). The plates were incubated for about two days to allow the cells to proliferate to confluence, and then maintained for another two days. The medium was changed to different differentiation media according to different experiments. The day of switching to differentiation medium was designated as day zero.

DMI Differentiation Model

The differentiation medium used in DMI differentiation model comprised an three-in-one differentiation inducer (DMI): dexamethasone (Sigma D-4902, dissolved in ethanol to produce a 0.25M stock solution), isobutyl-methylxanthine (Sigma I-5879, dissolved in DMSO to produce a 0.5M stock solution), and insulin (Sigma I-6634, dissolved in 0.01N HCl to produce a 10 mg/ml stock solution). The final concentrations of dexamethasone, isobutyl-methylxanthine and insulin were 0.25 μM, 0.5 mM and 5 μg/ml, respectively.

The four test compounds, Monasnicotinates A, B, C and D, were dissolved in DMSO respectively to produce a 5 mg/ml stock solution. One ml of the differentiation medium containing test sample was added to each well of the 24-well 3T3-L1 preadipocyte plates (the final concentration of the sample in each well was 5 μg/ml). The control group was the culture with only the differentiation medium and no sample. The cultures were incubated at 37° C. in a 5% CO$_2$ incubator for three days, and then the medium was replaced by DMEM with 10% FBS. The cultures were maintained until day 9 or day 10, and the amounts of triglyceride in the cells were analyzed. The extents of differentiation (the amounts of oil droplets) were also examined under an inverted microscope.

Insulin Differentiation Model

The differentiation medium used in insulin differentiation model was DMEM with 10% FBS comprising 10 μg/ml of insulin. Differentiation media containing each of the four test compounds, Monasnicotinates A, B, C and D, were added to each well of the 24- or 96-well 3T3-L1 preadipocyte plates (the final concentration of the test compounds in each well is 2 μg/ml). The control group was the culture with only the differentiation medium and no sample. The cultures were incubated at 37° C. in a 5% $CO_2$ incubator for seven days (during the period, the differentiation medium and sample were replaced with fresh ones twice), and then the medium was replaced by DMEM with 10% FBS. The cultures were maintained until day 9 or day 10. The cells of the experiment groups and control groups at day 9 or day 10 were stained with AdipoRed and the concentrations of triglyceride were analyzed.

(1) AdipoRed Staining

The 96-well plates were rinsed with PBS, and 200 μl of PBS and 5 μl of AdipoRed reagent (Lonze Walkersville, Inc., Walkersville, Md., USA, Catalog No. PT-7009) were added to each well. After 10 to 15 minutes, the plates were read with a spectrofluorometer (Infinite M200) set at an excitation wavelength of 485 nm and an emission wavelength of 572 nm. The fluorescent data of the experiment group was divided by the fluorescent data of the control group to obtain a percentage of induction activity.

(2) Measurement of Triglyceride Concentration

The 24-well plates were rinsed with PBS, and the cells were washed off with 0.1 ml of 1% Triton λ 100 per well. The cells were then frozen, thawed and centrifuged (10,000 rpm/5 min) and the supernatant were collected. An aliquot of 0.05 ml of the supernatant was analyzed using Triglycerol assay Kit (Audit Diagnostics, Ltd.).

The protein amounts were analyzed using Bio-Rad Dc Protein assay reagent (Bio-Rad). The triglyceride concentration was divided by the protein concentration obtained using Bio-Rad Dc Protein assay to calculated the amount (μg) of triglyceride per μg protein. The triglyceride amounts of the experiment groups were divided by those of the control groups to determine the differentiation induction activity of the samples.

Results

Figure 6:
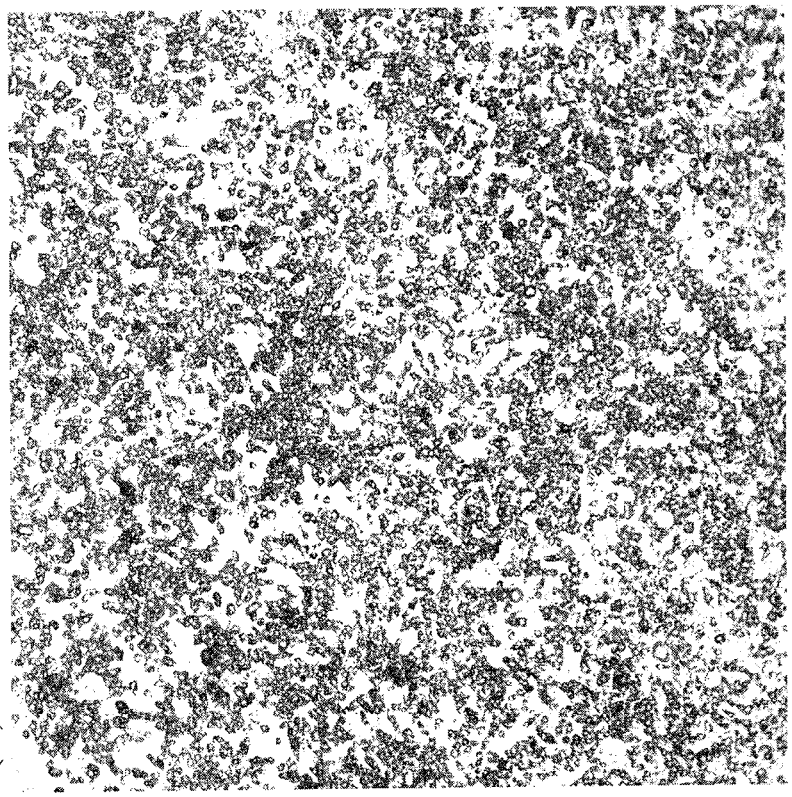
FIG. 6 shows the inverted microscope observation results in DMI differentiation model. Samples: (A) DMI control; (B) Monasnicotinate A (5 µg/ml); (C) Monasnicotinate B (5 µg/ml); (D) Monasnicotinate C (5 µg/ml); and (E) Monasnicotinate D (5 µg/ml).

FIGS. 6 (A) to (E) show the effects of Monasnicotinates A, B, C and D on the differentiation of 3T3-L1 preadipocytes in DMI differentiation model observed under an inverted microscope. The darker color indicates the abundance of triglyceride droplets present in differentiated adipocytes. It was found that the cultures treated with Monasnicotinates A, B, C and D contained more triglyceride droplets than the control culture, indicating that all four compounds can significantly promote the differentiation of 3T3-L1 preadipocytes.

The extents of enhancement of the test compounds on 3T3-L1 differentiation were shown in Table 1.

TABLE 1

Effects of Monasnicotinates A, B, C and D on the differentiation of 3T3-L1 preadipocytes

| | DMI model[a] | Insulin model[b] | |
|---|---|---|---|
| | TG (%) | AdipoRed (%) | TG (%) |
| Control | 100 | 100 | 100 |
| Monasnicotinate A | 159 | 159 | 128 |
| Monasnicotinate B | 175 | 287 | 132 |
| Monasnicotinate C | 132 | 209 | 145 |
| Monasnicotinate D | 204 | 247 | 169 |

[a]Sample concentration is 5 μg/ml.
[b]Sample concentration is 2 μg/ml.

It is found that all of the four test compounds, Monasnicotinates A, B, C and D, promote the differentiation of 3T3-L1 preadipocytes in both DMI and insulin models Example 6

Determination of NO Production and Cell Viability Assay

The murine macrophage cell line RAW264.7 (BCRC 60001=ATCC TIB-71) was cultured in Dulbecco's modified Eagle's medium (DMEM, Gibco BRL Life Technologies, Inc.) supplemented with 10% heat inactivated fetal bovine serum (FBS) and incubated at 37° C. in a humidified 5% $CO_2$ atmosphere with a 96-well flat-bottomed culture plate. After 24 hours, the condition medium was replaced with fresh DMEM and FBS. Then the three test compounds, Monasnicotinates A, C and D, (0, 1, 5, 10, and 20 μg/mL) were added respectively in the presence of lipopolysaccharide (LPS, 1 μg/mL; Sigma, Cat no: L-2654), and the plates were incubated at the same condition for 24 hours.

The cultured cells were then centrifuged and the supernatants were used for NO production measurement, with a MTT (3-(4,5-dimethylthiazol-2yl)-2,5-diphenyl tetrazolium bromide) assay to determine cell viability. The supernatant was mixed with an equal volume of the Griess reagent (1% sulfanilamide, 0.1% N-(1-naphthyl)ethyl-enediamine dihydrochloride in 2.5% phosphoric acid solution) and incubated for 10 min at room temperature. Nitrite concentration was determined by measuring the absorbance at 540 nm using an ELISA plate reader (μ Quant) (see Mosman, T., 1983, "Rapid colorimetric assay for cellular growth and survival: application to proliferation and cytotoxicity assays." *J. Immunol. Methods,* 65: 55-63). The MTT colorimetric assay was modified from that of Mosmann (see Johansson, M., et al., 2002, "Biologically active secondary metabolites from the ascomycete A111-95." *J. Antibiot.,* 55: 104-106). The test is based upon the selective ability of living cells to reduce the yellow soluble salt, MTT, to a purple-blue insoluble formazan. MTT (Merck; dissolved in phosphate-buffered saline at 5 mg/mL) solution was added onto the attached cells mentioned above (10 μl per 100 μl culture) and incubated at 37° C. for 4 hours. Then, DMSO was added and the amount of colored formazan metabolite formed was determined by absorbance at 550 nm. The optical density of formazan formed in control (untreated) cells was taken as 100% viability.

The inhibitory effects of Monasnicotinates A, C and D on the production of NO induced by LPS were evaluated. Monasnicotinates A and D showed inhibitory activity. The $IC_{50}$ of Monasnicotinate A is 5.72 μg/mL (16.0 μM) and the $IC_{50}$ of Monasnicotinate D is 9.4 μg/mL (24.8 μM). Monasnicotinates A and D showed stronger inhibition on NO production than quercetin, used as a positive control ($IC_{50}$ is 26.4 μM). Quercetin is reported to have an inhibitory effect on the production of NO by LPS-stimulated macrophage cells RAW264.7 ($IC_{50}$ is 26.8 µM) (see Motai, T. and Kitanaka, S., 2005, "Sesquiterpene chromones from *Ferula fukanensis* and their nitric oxide production inhibitory effects." *J. Nat. Prod.*, 68: 1732-1735). Cytotoxic effects of these compounds were measured using MTT assay. Monasnicotinates A (1-10 µg/mL) and D (1-20 µg/mL) did not show any significant cytotoxicity with LPS treatment for 24 hours. Monasnicotinate C showed significant cytotoxic effect at 10 µg/mL.

Example 7

Red Yeast Rice Extracts Enhanced the Differentiation of 3T3-L1 Cells

Red yeast rice was prepared according to the method described in Examples 1 and 2 using *Monascus pilosus* BCRC 930117 (DSM 22351) and *Monascus purpureus* M615 BCRC 930146 (DSM 24162).

Preparation of organic solvent extracts: The solid fermented red yeast rice (1 g for each red yeast rice) was added to a 50 ml serum bottle and 25 ml of organic solvent (methanol, ethanol or ethyl acetate) were added to each bottle. The red yeast rice was extracted by rotating the bottles on a suspension mixer with a low speed at room temperature over night. The extracted fluids were filtrated with filter paper and the solvents in the filtrated fluids were removed using vacuum dryer to give dried methanol, ethanol and ethyl acetate extracts of BCRC 930117- and BCRC 930146-fermented rice.

Preparation of water extracts: The solid fermented red yeast rice (5 g for each red yeast rice) was added to a 500 ml serum bottle and 250 ml of de-ionized water were added to each bottle. The red yeast rice was extracted by heating the bottles on a stir heater at 100° C. for 60 minutes. The extracted fluids were filtrated by filter paper and the solvents in the filtrated fluids were removed using freeze dryer to give dried water extracts of BCRC 930117- and BCRC 930146-fermented rice.

The dried water extracts prepared in the above were dissolved in de-ionized water, and the dried methanol, ethanol and ethyl acetate extracts were dissolved in dimethyl sulfoxide (DMSO) to give 2 or 5 mg/ml stock samples. Media with different concentrations of the extracts were prepared for 3T3-L1 preadipocytes differentiation assay.

3T3-L1 preadipocytes differentiation assay was conduct according to Example 5. The results were shown in Tables 2 and 3.

TABLE 2

Effects of Methanol and Water Extracts of BCRC 930117- and BCRC 930146-Fermented Rice on the Differentiation of 3T3-L1 Preadipocytes

| | Final conc. (µg/ml) | AdipoRed (% of control) | TG (% of control) |
|---|---|---|---|
| DMI model MeOH extract | | | |
| BCRC 930146 | 5 | 189 ± 19 | 171 ± 23 |
| | 10 | 243 ± 42 | 143 ± 12 |
| BCRC 930117 | 5 | 212 ± 37 | 152 ± 8 |
| | 10 | 204 ± 39 | 122 ± 4 |
| $H_2O$ extract | | | |
| BCRC 930146 | 10 | 139 ± 32 | 105 ± 25 |
| | 40 | 145 ± 38 | 94 ± 3 |
| BCRC 930117 | 10 | 147 ± 42 | 133 |
| | 40 | 173 ± 49 | 101 |
| Insulin model MeOH extract | | | |
| BCRC 930146 | 5 | 118 ± 24 | 102 ± 13 |
| | 10 | 151 ± 23 | 124 ± 0 |
| BCRC 930117 | 5 | 123 ± 19 | 97 |
| | 10 | 130 ± 15 | 115 ± 2 |
| $H_2O$ extract | | | |
| BCRC 930146 | 10 | 94 ± 15 | 111 ± 12 |
| | 40 | 105 ± 18 | 88 ± 6 |
| BCRC 930117 | 10 | 108 ± 21 | 130 |
| | 40 | 110 ± 10 | 110 |

TABLE 3

Effects of Methanol, Ethanol and Ethyl Acetate Extracts of BCRC 930146-Fermented Rice on the Differentiation of 3T3-L1 Preadipocytes

| | Final conc. (µg/ml) | AdipoRed (% of control) | TG (% of control) |
|---|---|---|---|
| Insulin model | | | |
| MetOH extract | 5 | 118 | 117 |
| | 10 | 151 | 133 |
| EtOH extract | 5 | 170 | 124 |
| | 10 | 213 | 152 |
| EA extract | 5 | 165 | 130 |
| | 10 | 168 | 144 |
| DMI model | | | |
| MetOH extract | 5 | 189 | ND |
| | 10 | 243 | ND |
| EtOH extract | 5 | 241 | ND |
| | 10 | 312 | ND |
| EA extract | 5 | 217 | ND |
| | 10 | 598 | ND |

ND: not detected

The results of Tables 2 and 3 demonstrate that methanol extracts of BCRC 930117- and BCRC 930146-fermented red yeast rice can significantly enhance the differentiation of 3T3-L1 preadipocytes in both DMI model and insulin model. The ethanol and ethyl acetate extracts of BCRC 930146-fermented red yeast rice can also significantly enhance the differentiation of 3T3-L1 preadipocytes.

Example 8

Monasnicotinates A, B, C and D Increase PPARγ Expression and Adiponectin Concentration in Differentiated 3T3-L1 Cells 3T3-L1 cells were treated with Monasnicotinates A, B, C and D (prepared in Example 3) as described in Example 5. Nuclear and cytosolic proteins of the differentiated 3T3-L1 cells were extracted and the nuclear PPARγ and cytosolic adiponectin contents were analyzed using commercial kits.

(1) Nuclear and Cytosolic Proteins Extraction

3T3-L1 cells were incubated and differentiated on petri dish (9 cm) for 9 days and washed with PBS. 1 ml of buffer A working solution (Affymetrix® Nuclear Extraction Kits, Panomics, Inc.; freshly prepared according to the instructions) was added to the petri dish, and the petri dish was placed on ice and shaken for 10 minutes on a shaker. Cells on the petri dish were transferred to a 1.5 ml centrifuge tube and centrifuged at 14,000 rpm for 3 minutes. The supernatant, the cytosol fraction, was collected for further analysis. 0.5 ml of buffer B working solution (Affymetrix® Nuclear Extraction Kits, Panomics, Inc.; freshly prepared according to the instructions) was added to the centrifuge tube to re-suspend the cell pellet and the centrifuge tube was placed on ice and shaken for two hours on a shaker. The centrifuge tube was then centrifuged at 14,000 rpm for 5 minutes. The supernatant, the nucleus fraction, was collected for further analysis.

(2) Nuclear PPARγ ELISA

Nuclear PPARγ in the nucleus fraction was analyzed using Transcription Factor PPARγ ELISA Kit (Panomics, Inc.) according to the instructions.

(3) Cytosolic Adiponectin (AdipoO) ELISA

Cytosolic adiponectin in the cytosol fraction was analyzed using Quantikine Mouse Adiponectin immunoassay (R&D systems) according to the instructions.

Figure 7:
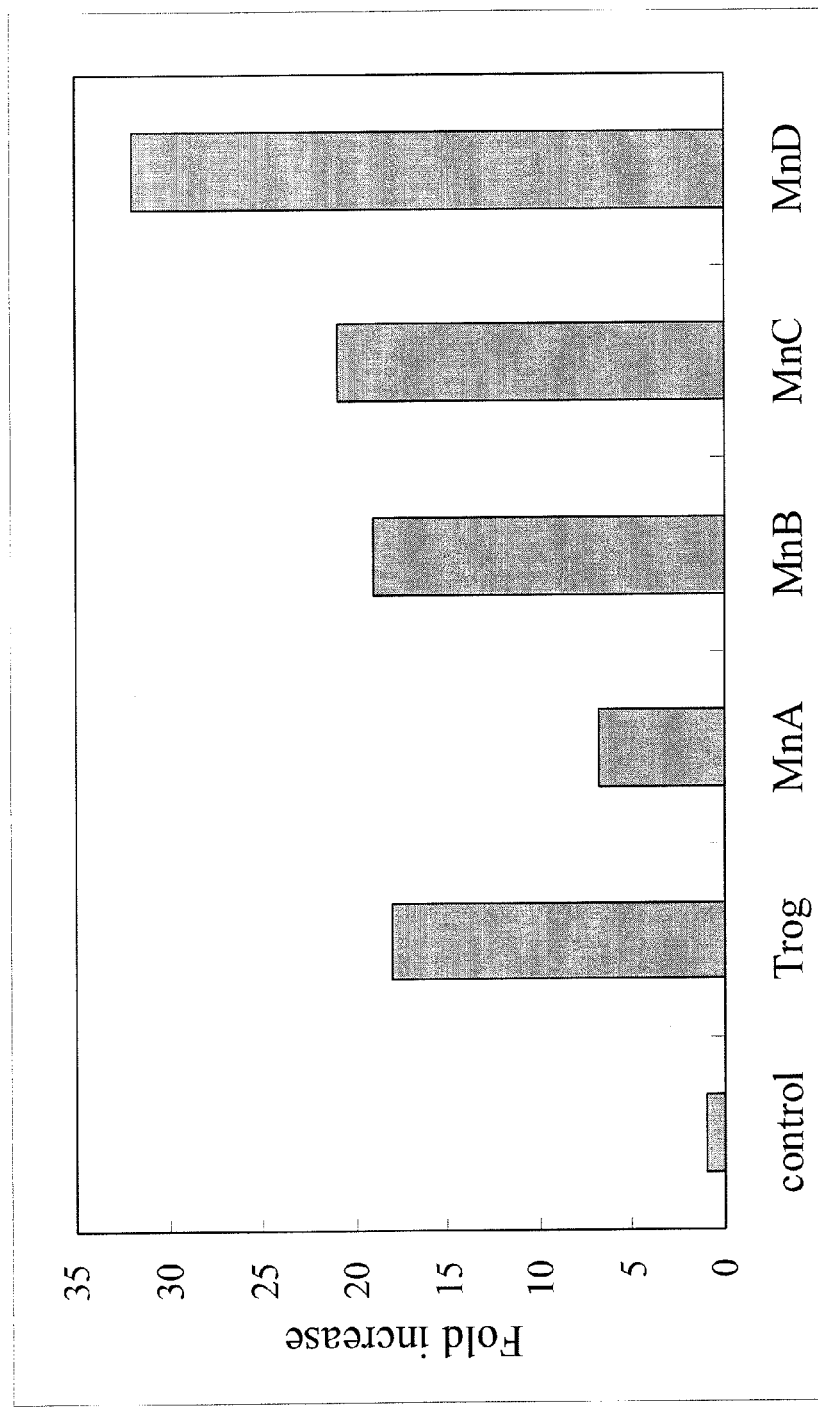
FIG. 7 shows that Monasnicotinate A-D increased the expression of cytosolic adiponectin of 3T3-L1 adipocytes in insulin model (A) and DMI model (B). Control: medium only; Trog: troglitazone at 200 nM. The final sample concentrations were at 5 µg/mL.
Figure 7:
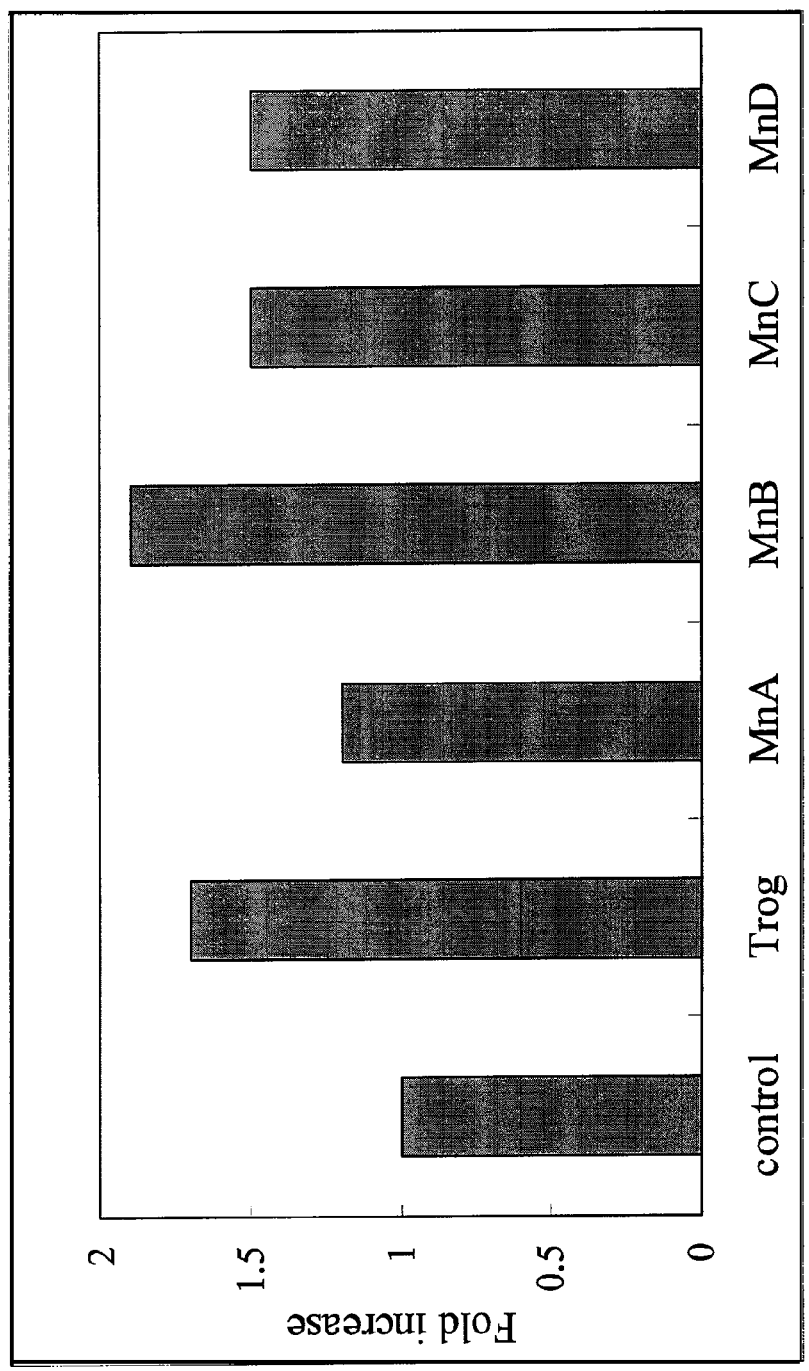

The results show that Monasnicotinates A, B, C and D can increase the expression of nuclear PPARγ (see Table 4) and the concentration of cytosolic adiponectin in 3T3-L1 cells (see FIGS. 7 (A) and (B)).

TABLE 4

Effects of Monasnicotinates A, B, C and D on PPARγ Expression of 3T3-L1

|  | Insulin model | DMI model |
|---|---|---|
|  | PPARγ expression (% of control) | |
| Troglitaozne | 184 ± 12 | 185 ± 17 |
| Monasnicotinate A | 139 ± 1 | 100 ± 7 |
| Monasnicotinate B | 237 ± 9 | 147 ± 2 |
| Monasnicotinate C | 333 ± 15 | 115 ± 1 |
| Monasnicotinate D | 424 ± 19 | 166 ± 5 |

Control: medium only.
Final sample concentrations were at 5 μg/mL, troglitaozne at 200 nM.

Example 9

Monasnicotinates A, B, C and D and Red Yeast Rice Extracts Demonstrated PPARs Binding Activity Monasnicotinates A, B, C and D were prepared according to Example 3 and Ethanol and ethyl acetate extracts of BCRC 930146-fermented rice were prepared according to Example 7. The binding activity of Monasnicotinates A, B, C and D and ethanol and ethyl acetate extracts of BCRC 930146-fermented rice to PPARγ and PPARα were analyzed using competitive binding assay kits (LanthaScreen TR-FRET PPARγ Binding Assay and Invitrogen PPARα Competitive Binding Assay) according to their instructions. Troglitazone and arachidonic acid were used as reference substances for PPARγ and PPARα ligand, respectively.

Table 5 shows that Monasnicotinates A, B, C and D and ethanol and ethyl acetate extracts of BCRC 930146-fermented rice have PPARγ binding activity and ethanol and ethyl acetate extracts of BCRC 930146-fermented rice have PPARα binding activity.

TABLE 5

PPARs Binding Activities of Ethanol and Ethyl Acetate Extracts of BCRC 930146-Fermented Rice and Monasnicotinates A, B, C and D

|  | PPARγ binding | PPARα binding |
|---|---|---|
|  | $IC_{50}$ (μg/ml) | |
| EtOH extract | 6.01 | 25.7 |
| EA extract | 4.72 | 9.2 |
| Monasnicotinate A | 15.0 | $ND^c$ |
| Monasnicotinate B | 4.1 | ND |
| Monasnicotinate C | 7.0 | ND |
| Monasnicotinate D | 23.2 | ND |

ND: not detectable

Example 10

Effects of Red Yeast Rice Extracts on High Fat/High Sucrose Diet-Induced Obese and Hyperglycemic Mice Preparation of Red Yeast Rice Ethanol Extracts Red yeast rice was prepared according to the method described in Examples 1 and 2 using *Monascus purpureus* M615 BCRC 930146 (DSM 24162). 2.4 Kg of BCRC 930146-fermented rice were added to a 10 L stainless steel container, and 3 L of 95% ethanol solution were added to the container. The mixture was incubated at room temperature for 72 hours and the filtered with filter paper. The solvents in the filtrated fluids were removed using vacuum dryer to give 0.64 L concentrated fluids. 0.16 L of 2.5% methylcellulose was added to the concentrated fluids, and the mixture as freeze dried to give 110 g of dried extracts. The dried extracts were ground to give the powder extracts for the animal tests.

Animal Test

Male C57BL/6JNarl mice were fed with high fat/high sucrose feed for four weeks to induce obesity and hyperglycemia. The non-fasting plasma glucose concentration of HF/HS mice is higher than normal mice (128.9±10.4 mg/dL vs. 154.1±16.1 mg/dL, $p<10^{-3}$). HF/HS mice were divided into four groups (one control group and three test groups treated with different doses of red yeast rice ethanol extracts). The mice in the three test groups were administered with 277 mg/kg body weight (low), 554 mg/kg body weight (medium) and 1108 mg/kg body weight (high) of red yeast rice ethanol extracts. The mice in control group were administered with the ethanol extracts prepared from rice fermented without BCRC 930146 by the same processes described in Examples 1 and 2 and the same extraction process described in Example 7. The mice were treated for ten weeks. Oral glucose tolerance test was conducted at week eight and insulin tolerance test was conducted at week ten. The mice were sacrificed at 11 weeks after fasting; bloods were collected for hematological analysis, epididymal adipose tissues were fixed, embedded and sliced, and the size and number of adipocytes were calculated.

Results

Table 6 shows the results of oral glucose tolerance test after eight weeks of treatment. The results show that the plasma glucose concentrations at 30 minutes and 120 minutes and the $AUC120_{min}$ of the three test groups were significantly lower than that of HF/HS control group ($p<0.05$).

TABLE 6

Results of Glucose Tolerance Test after 8 weeks of Treatment
of Ethanol Extracts of BCRC 930146-Fermented Rice

|  | Plasma glucose (mg/dL) | | | | $AUC_{120\ min}$ |
|---|---|---|---|---|---|
|  | 0 min | 30 min | 60 min | 120 min | (mg/dl · min) |
| Normal (n = 9) | 72.9 ± 6.2 | 327.7 ± 70.5 | 219.6 ± 48.9 | 148.8 ± 34.9 | 26363 ± 4761 |
| HF/HS (n = 11) | 84.3 ± 6.0† | 398.0 ± 63.2† | 299.8 ± 78.7† | 151.9 ± 16.8† | 32515 ± 5299† |
| Low (n = 10) | 78.9 ± 8.6 | 337.7 ± 44.4* | 242.9 ± 51.2 | 150.7 ± 32.4 | 27948 ± 3456* |
| Medium (n = 10) | 79.7 ± 7.0 | 338.8 ± 57.8* | 241.6 ± 41.9 | 145.3 ± 12.5 | 27785 ± 3309* |
| High (n = 10) | 75.3 ± 5.0* | 335.7 ± 50.8* | 250.0 ± 51.5 | 132.3 ± 23.9 | 27547 ± 3355* |

The results were represents by mean ± sd.
† and * indicate p < 0.05 compared to normal and HF/HS, respectively.

Table 7 shows the results of insulin tolerance test after ten weeks of treatment. The results show that the plasma glucose concentrations at 15 minutes and 60 minutes and the $AUC_{60min}$ of the medium dose group and high dose group were significantly lower than that of HF/HS control group (p<0.05).

TABLE 7

Results of Insulin Tolerance Test after 10 weeks of Treatment
of Ethanol Extracts of BCRC 930146-Fermented Rice

|  | Plasma glucose (mg/dL) | | | | $AUC_{60\ min}$ |
|---|---|---|---|---|---|
|  | 0 min | 15 min | 30 min | 60 min | (mg/dl · min) |
| Normal (n = 10) | 123.2 ± 13.2 | 89.2 ± 11.5 | 83.3 ± 7.9 | 99.3 ± 11.9 | 5132 ± 206 |
| HF/HS (n = 11) | 171.8 ± 20.6† | 118.7 ± 29.4† | 97.3 ± 14.0† | 81.9 ± 10.4† | 6486 ± 828† |
| Low (n = 10) | 175.5 ± 16.9 | 107.6 ± 17.6 | 97.6 ± 14.5 | 72.9 ± 12.7 | 6220 ± 468 |
| Medium (n = 10) | 165.6 ± 23.6 | 98.3 ± 13.4* | 89.9 ± 13.7 | 66.2 ± 16.0* | 5734 ± 644* |
| High (n = 10) | 155.6 ± 23.6 | 96.3 ± 20.9* | 85.0 ± 14.6 | 68.5 ± 15.4* | 5753 ± 666* |

The results were represents by mean ± sd.
† and * indicate p < 0.05 compared to normal and HF/HS, respectively.

Results of hematological analysis at week 11 are shown in Table 8.

The results show that (1) the insulin concentrations of three test groups were significantly lower than that of HF/HS control group; (2) both medium and high dose treatments can significantly decrease fasting plasma glucose concentrations; (3) the plasma HDL concentrations of both low and high dose groups were significantly higher than that of HF/HS control group; and (4) the HDL/TC ratios of three test groups were significantly elevated.

TABLE 8

Results of Hematological Analysis

|  | Plasma insulin (g/L) | Plasma glucose (mg/dL) | Total cholesterol (TC) (mg/dL) | High-density lipoproteins (HDL) (mg/dL) | HDL/TC |
|---|---|---|---|---|---|
| Normal (n = 10) | 0.226 ± 0.066 | 136.8 ± 33.3 | 98.8 ± 9.9 | 88.8 ± 8.6 | 0.89 ± 0.02 |
| HF/HS (n = 9) | 1.926 ± 1.144† | 182.2 ± 17.0† | 174.6 ± 6.2† | 148.9 ± 2.9† | 0.86 ± 0.02† |
| Low (n = 10) | 0.746 ± 0.403* | 164.5 ± 21.6 | 180.3 ± 12.8 | 159.5 ± 11.8* | 0.88 ± 0.02* |
| Medium (n = 12) | 0.377 ± 0.278* | 157.3 ± 28.3* | 162.0 ± 13.0* | 148.5 ± 15.2 | 0.89 ± 0.05* |
| High (n = 11) | 0.678 ± 0.335* | 153.8 ± 38.1* | 179.2 ± 11.9 | 163.1 ± 8.8* | 0.91 ± 0.06* |

The results were represents by mean ± sd.
† and * indicates p < 0.05 compared to normal and HF/HS, respectively.

In summary, red yeast rice ethanol extracts can improve glucose intolerance and insulin resistance, and can improve the lipid profile in blood and elevate the HDL/TC ratio.

Figure 8:
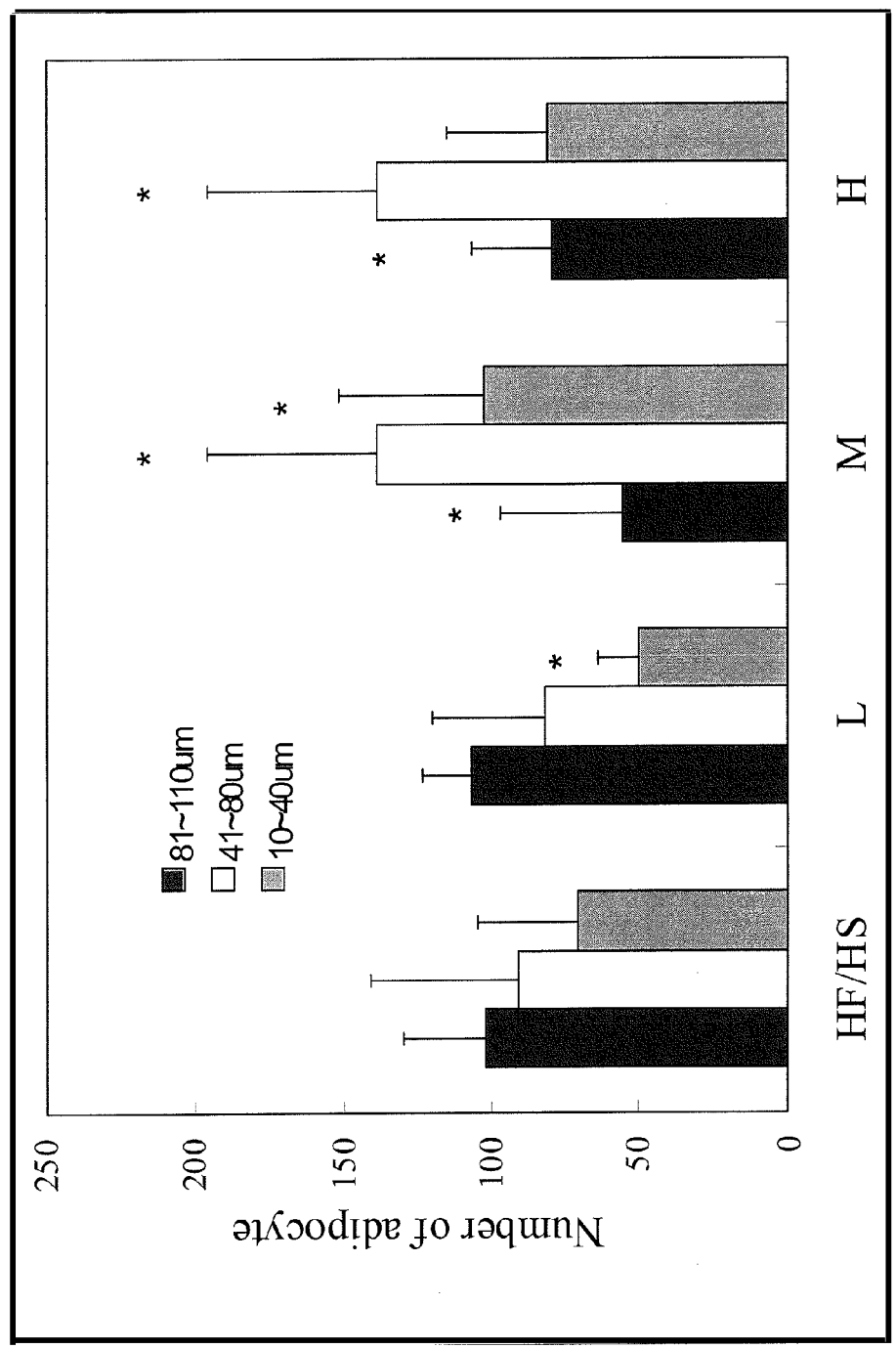
FIG. 8 shows the size distribution of adipocytes in C57BL/6JNarl mice after feeding ethanol extracts of red yeast rice. * indicates significant differences between test groups and HF/HS group (P<0.05).

FIG. 8 shows the size distribution of adipocytes in epididymal adipose tissues. The numbers of large adipocytes (81-110 μm in diameter) in high dose group is significantly lower than that of control group. The numbers of medium adipocytes (10-40 μm in diameter) and small adipocytes (10-40 μm in diameter) in medium and high dose groups are significantly higher than that of control group. Although the total numbers of adipocytes of control group and the three test groups are not significantly different, high dose group has less large adipocytes and more medium and small adipocytes. It is known in the art that part of the effect of PPARγ agonist on improving insulin resistance is achieved by enhancing the differentiation of preadipocytes. The results of the present invention demonstrate that the effect of ethanol extracts of red yeast rice on the increase of functional medium and small adipocytes may be achieved via the enhancement of the differentiation of preadipocytes by Monasnicotinates A, B, C or D, which has PPARs binding activity.

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. A pharmaceutical composition comprising: (a) an isolated compound consisting of formula (I):

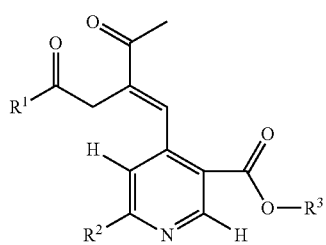

or a pharmaceutically acceptable salt thereof,
wherein $R^1$ is alkyl, $R^2$ is alkyl or alkenyl, and $R^3$ is alkyl, and (b) a pharmaceutically acceptable carrier or excipient, wherein the compound is incorporated into the pharmaceutical composition as a purified compound, wherein the composition is in a form selected from the group consisting of an emulsion, a tablet, a pill, a capsule, a sustained release formulation, an ampoule, and a combination thereof, and wherein the pharmaceutically acceptable carrier or excipient is selected from the group consisting of citrate buffer, phosphate buffer, acetate buffer, bicarbonate buffer, stearic acid, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, a cellulosic material, low melting wax cocoa butter, amino acids, urea, ascorbic acid, phospholipids, proteins, ethylenediamine tetraacetic acid (EDTA), dimethyl sulfoxide (DMSO), sodium chloride or other salts, liposomes, mannitol, sorbitol, glycerol or powder, and a polymer.

2. The pharmaceutical composition of claim 1, wherein $R^1$ is $C_1$-$C_{10}$alkyl, $R^2$ is $C_1$-$C_6$alkyl or $C_2$-$C_6$alkenyl, and $R^3$ is $C_1$-$C_6$alkyl.

3. The pharmaceutical composition of claim 1, wherein $R^1$ is pentyl, $R^2$ is propenyl, and $R^3$ is methyl.

4. The pharmaceutical composition of claim 1, wherein $R^1$ is pentyl, $R^2$ is propenyl, and $R^3$ is ethyl.

5. The pharmaceutical composition of claim 1, wherein $R^1$ is heptyl, $R^2$ is propenyl, and $R^3$ is methyl.

6. The pharmaceutical composition of claim 1, wherein $R^1$ is pentyl, $R^2$ is propyl, and $R^3$ is methyl.

7. The pharmaceutical composition of claim 1, wherein the compound is methyl-4-((E)-2-acetyl-4-oxonon-1-enyl)-6-((E)-prop-1-enyl)nicotinate (Monasnicotinate A), ethyl-4-((E)-2-acetyl-4-oxonon-1-enyl)-6-((E)-prop-1-enyl)nicotinate (Monasnicotinate B), methyl-4-((E)-2-acetyl-4-oxoundec-1-enyl)-6-((E)-prop-1-enyl) nicotinate (Monasnicotinate C), or (E)-methyl-4-(2-acetyl-4-oxonon-1-enyl)-6-propylnicotinate (Monasnicotinate D) or a pharmaceutically acceptable salt-thereof.

8. The pharmaceutical composition of claim 1, wherein the form of the composition is an emulsion.

9. The pharmaceutical composition of claim 1, wherein the form of the composition is selected from the group consisting of a tablet, a pill, a capsule, a sustained release formulation, and an ampoule.

10. The pharmaceutical composition of claim 1, wherein the form of the composition is a tablet, a pill, an ampoule or a capsule.

11. The pharmaceutical composition of claim 1, wherein the composition is in the form of a sustained release formulation.

12. The pharmaceutical composition of claim 1, wherein the composition consists of the isolated compound of formula (I) or a pharmaceutically acceptable salt thereof and the pharmaceutically acceptable carrier or excipient.

13. A method of making the isolated compound of claim 1, comprising:
    (a) fermenting rice with an isolated strain of Monascus spp. to obtain red yeast rice;
    (b) extracting the red yeast rice with methanol or ethanol to provide an extract;
    (c) partitioning the extract obtained in step (b) between ethyl acetate and water to obtain an ethyl acetate-soluble fraction;
    (d) eluting the ethyl acetate-soluble fraction through a silica gel chromatography column to provide an eluted fraction;
    (e) purifying the eluted fraction of (d) with a silica gel chromatography column and/or preparative thin layer chromatography (TLC) to obtain the isolated compound.

14. The method of claim 13, wherein the isolated strain is Monascus pilosus BCRC 930117 (DSM 22351) or Monascus purpureus M615 BCRC 930146 (DSM 24162).

15. The method of claim 13, wherein the isolated strain of Monascus is Monascus pilosis or Monascus purpureus.

16. A method of treating hyperlipidemia, obesity, insulin resistance and/or glucose intolerance in a subject in need thereof, comprising administering the composition of claim 1, wherein said composition comprises and effective amount of the isolated compound of formula (I).

17. The method of claim 16, wherein a second therapeutic agent for treating metabolic syndrome is administered to the subject.

18. The method of claim 17, wherein the second therapeutic agent is selected from the group consisting of statins, fibrates, nicotinic acid; diuretics, angiotensin-converting enzyme (ACE) inhibitors; metformin, insulin, sulfonylurea (SU), biguanide, α-glucosidase inhibitors and thiazolidinediones (TZDs).

19. The pharmaceutical composition of claim 1, wherein said isolated compound is the compound of formula (I).

20. The pharmaceutical composition of claim 1, wherein said isolated compound is the pharmaceutically acceptable salt of the compound of formula (I).

21. The pharmaceutical composition of claim 1, further comprising a second therapeutic agent for treating metabolic syndrome.

22. The pharmaceutical composition of claim 21, wherein the second therapeutic agent is selected from the group consisting of statins, fibrates, nicotinic acid; diuretics, angiotensin-converting enzyme (ACE) inhibitors; metformin, insulin, sulfonylurea (SU), biguanide, α-glucosidase inhibitors and thiazolidinediones (TZDs).

23. The pharmaceutical composition of claim 21, wherein the composition consists of the isolated compound of formula (I) or a pharmaceutically acceptable salt thereof, the second therapeutic agent and the pharmaceutically acceptable carrier or excipient.

\* \* \* \* \*